US009981908B2

(12) United States Patent
Marelli et al.

(10) Patent No.: US 9,981,908 B2
(45) Date of Patent: May 29, 2018

(54) AMINO ACID DERIVATIVES

(71) Applicant: MedImmune Limited, Cambridge (GB)

(72) Inventors: Marcello Marelli, Gaithersburg, MD (US); Michael van Brunt, Covington, WA (US); Kenneth H. Grabstein, Mercer Island, WA (US)

(73) Assignee: MedImmune Limited, Cambridge (GB)

( * ) Notice: Subject to any disclaimer, the term of this patent is extended or adjusted under 35 U.S.C. 154(b) by 0 days. days.

(21) Appl. No.: 14/910,107

(22) PCT Filed: Aug. 4, 2014

(86) PCT No.: PCT/IB2014/002505
§ 371 (c)(1),
(2) Date: Feb. 4, 2016

(87) PCT Pub. No.: WO2015/019192
PCT Pub. Date: Feb. 12, 2015

(65) Prior Publication Data
US 2016/0176811 A1    Jun. 23, 2016

Related U.S. Application Data

(60) Provisional application No. 61/862,497, filed on Aug. 5, 2013.

(51) Int. Cl.
| | |
|---|---|
| *C07C 323/58* | (2006.01) |
| *C07C 271/12* | (2006.01) |
| *C07C 271/16* | (2006.01) |
| *C07C 271/20* | (2006.01) |
| *C07C 271/22* | (2006.01) |
| *C07C 275/10* | (2006.01) |
| *C07C 275/14* | (2006.01) |
| *C07C 275/16* | (2006.01) |
| *C07C 235/06* | (2006.01) |
| *C07C 247/04* | (2006.01) |
| *C07K 16/32* | (2006.01) |
| *C07C 275/20* | (2006.01) |

(52) U.S. Cl.
CPC .......... *C07C 323/58* (2013.01); *C07C 235/06* (2013.01); *C07C 247/04* (2013.01); *C07C 271/12* (2013.01); *C07C 271/16* (2013.01); *C07C 271/20* (2013.01); *C07C 271/22* (2013.01); *C07C 275/10* (2013.01); *C07C 275/14* (2013.01); *C07C 275/16* (2013.01); *C07C 275/20* (2013.01); *C07K 16/32* (2013.01); *C07K 2317/24* (2013.01); *C07K 2317/40* (2013.01); *C07K 2317/526* (2013.01)

(58) Field of Classification Search
None
See application file for complete search history.

(56) References Cited

U.S. PATENT DOCUMENTS

| | | | |
|---|---|---|---|
| 3,711,458 | A | 1/1973 | Olofson et al. |
| 4,512,979 | A | 4/1985 | Patchett |
| 5,216,023 | A | 6/1993 | Literati et al. |
| 2010/0304431 | A1 | 12/2010 | Yokoyama et al. |
| 2012/0077948 | A1 | 3/2012 | Nguyen et al. |
| 2014/0127209 | A1 | 5/2014 | Grabstein et al. |
| 2015/0251994 | A1 | 9/2015 | Grabstein et al. |
| 2015/0259721 | A1 | 9/2015 | Grabstein et al. |
| 2016/0024522 | A1 | 1/2016 | Dieci et al. |

FOREIGN PATENT DOCUMENTS

| | | |
|---|---|---|
| WO | WO 2010/139948 A2 | 12/2010 |
| WO | WO 2011/044255 A1 | 4/2011 |
| WO | WO 2014/036492 A1 | 3/2014 |

OTHER PUBLICATIONS

CAS No. 41889-04-7, Entered in STN Nov. 16, 1984, 1 pg.*
CAS No. 170023-91-3, Entered in STN Nov. 10, 1995, 1 pg.*
CAS No. 174851-27-5, Entered in STN Apr. 9, 1996, 1 pg.*
Eck et al., "dl-Lysine Hydrochlorides," Organic Syntheses, Coll. vol. 2, p. 374 (1943); vol. 19, p. 61, (1939).*
Li et al., "Ligand-Free Palladium-Mediated Site-Specific Protein Labeling Inside Gram-Negative Bacterial Pathogens," J. Am. Chem. Soc. 2013, 135, 7330-7338.*
Mukai, Takahito et al., 2008, "Adding L-lysine derivatives to the genetic code of mammalian cells with engineered pyrrolysly-tRNA synthetases", Biochemical and Biophysical Research Communications, 371:818-822.
Fekner, T. et al., 2010, "Pyrrolysine Analogs for Translational Incorporation into Proteins", European Journal of Organic Chemistry, 4171-4179.
Kavran, J.M. et al., 2007, "Structure of pyrrolysyl-tRNA synthetase, an archaeal enzyme for genetic code innovation", PNAS, 104(27):11268-11273.
Kobayashi, Takatsugu et al., 2009, "Recognition of Non-a-amino Substrates by Pyrrolysyl-tRNA Synthetase", Journal of Molecular Biology, 385:1352-1360.
Liu, Chang C. et al., 2010, "Adding New Chemistries to the Genetic Code", Annual Review of Biochemistry, 413-444.
Nguyen, Duy P. et al., 2009, "Genetic Encoding and Labeling of Aliphatic Azides and Alkynes in Recombinant Proteins via a Pyrrolysyl-tRNA Synthetase/tRNACUA Pair and Click Chemistry", Journal of the American Chemistry Society, 8720-8721.
Yanagisawa, Tatsuo et al., 2008, "Crystallographic Studies on Multiple Conformational States of Active-site Loops in Pyrrolysyl-tRNA Synthetase", Journal of Molecular Biology, 378:634-62.

(Continued)

*Primary Examiner* — Pancham Bakshi
*Assistant Examiner* — Mark R Luderer

(57) ABSTRACT

There are provided pyrrolysine analogs of the formulae (X), (I), (II), (V), (VI), (VII) and (VIII), in which the a, b, d, X, Y, Z, FG, R, $R_1$, $R_2$ and $R_3$ are as defined in the claims, which are useful in bioconjugation processes and mutant proteins containing them.

26 Claims, 1 Drawing Sheet

(56) References Cited

OTHER PUBLICATIONS

Yanagisawa, Tatsuo et al., 2008, "Multistep Engineering of Pyrrolysyl-tRNA Synthetase to Genetically Encode Ne-(o-Azidobenzyloxycarbonyl) lysine for Site-Specific Protein Modification", Chemistry & Biology, 1187-1197.

Yanagisawa, T. et al., 2013, "A novel crystal form of pyrrolysyl-tRNA synthetase reveals the pre- and post-aminocyl-tRNA synthesis conformational states of the adenylate and aminoacyl moieties and an asparagine residue in the catalytic site", Acta Crystallographica Section D, Biological Crystallography, D69. 5-15.

Spanton, et al., 1982, Chemical Defense and Self Defense: Biochemical Transformations of Contact Insecticides Produced by Soldier Termites, Tetrahedron, 38(13):1921-1930.

Li, Jie et al., 2013, "Ligand-Free Palladium-Mediated Site-Specific Protein Labeling Inside Gram-Negative Bacterial Pathogens", Journal of the American Chemical Society, 135(19)7330-7338.

Vrabel, Milan et al., 2011, "Optimization of the Posttranslational Click Modification of Proteins", Collection of Czechoslovak Chemical Communications, 76(9):1089-1101.

Plass, Tilman et al., 2011, "Genetically Encoded Copper-Free Click Chemistry", Angewandte Chemie, International Edition, 50(17):3878-3881.

Ledger, R. et al., 1965, "The Use of Sequestering Agents in the Preparation of ε-Acyl-L-lysine and δ-Acyl-L-ornithine Derviatives", Australian Journal of Chemstry, 18(6):933-935.

Erickson, B.W. et al., 1973, "Use of Chlorinated Benzyloxycarbonyl Protecting Groups to Eliminate $N^\epsilon$-Branching at Lysine during Solid-Phase Peptide Synthesis", Journal of the American Chemical Society, 95(11):3757-3763.

Matsui, Katsuhiko, 1967, Studies on Acylse Activity and Microoganisms. Properties of δ-Ornithine Acylase (5-N-Acylornithine Amidohydrolase), Chemical and Pharmaceutical Bulletin, 15(1), 1586-1596.

Noda, Kosaku et al., 1970, "Modified Benzyloxycarbonyl Groups for Protection of ε-Amino Group of Lysine", Bulletin of the Chemical Society of Japan, 43:1883-1885.

Theodoropoulos, Dimitrios, 1958, "Synthesis of ε-Peptides of Lysine", Journal of Organic Chemistry, 23(1):140.

R. Popovitz-Biro et al., 1990, "A New Series of Amphiphilic Molecules Forming Stable Z-Type (Polar) Langmuir-Blodgett Films", Journal of American Chemical Society, 1990,112(7):2498-2506.

Coward, James K. et al., 1972, "Analogs of S-Adenosylhomocysteine as Potential Inhibitors of Biological Transmethylation. Synthesis and Biological Activity of Homocysteine Derivatives Bridged to Adenine", Journal of Medicinal Chemistry, 15(4):381-384.

Kimbonguila, André Malanda et al., 1999, "Allylic Protection of Thiols and Cysteine: I: The Allyloxycarbonylaminomethyl Group", Tetrahedron, 55(22):6931-6944.

Li, Xin et al., 2010, "$N^6$-(2-(R)-Propargylglycyl)lysine as a Clickable Pyrrolysine Mimic", Chemistry, An Asian Journal, 5(8):1765-1769.

Zhang, Henry Q. et al., 1997, "Mechanism of Inactivation of Neuronal Nitric Oxide Synthase by $N^\omega$-Allyl-l-Arginine", Journal of the American Chemical Society, 119(45):10888-10902.

Lindley, H. et al., 1959, "The Preparation of Compounds Related to S-2-Aminoethyl-L-Cysteine", Australian Journal of Chemistry, 12(2):296-298.

Jermyn, M.A., 1966, "Carbobenzoxy Derivatives of S-Aminoalkyl-L-Cysteines", Aust. J. Chem., 19(10):1999-2000.

Nishino, Norikazu, et al., 1996, "Tandem Enzymatic Resolution Yielding L-α-Aminoalkanedioic Acid ω-Esters", Chem. Pharm. Bull., 44(1):212-214.

Written Opinion for PCT/IB2014/002505 dated Jul. 4, 2015.

* cited by examiner

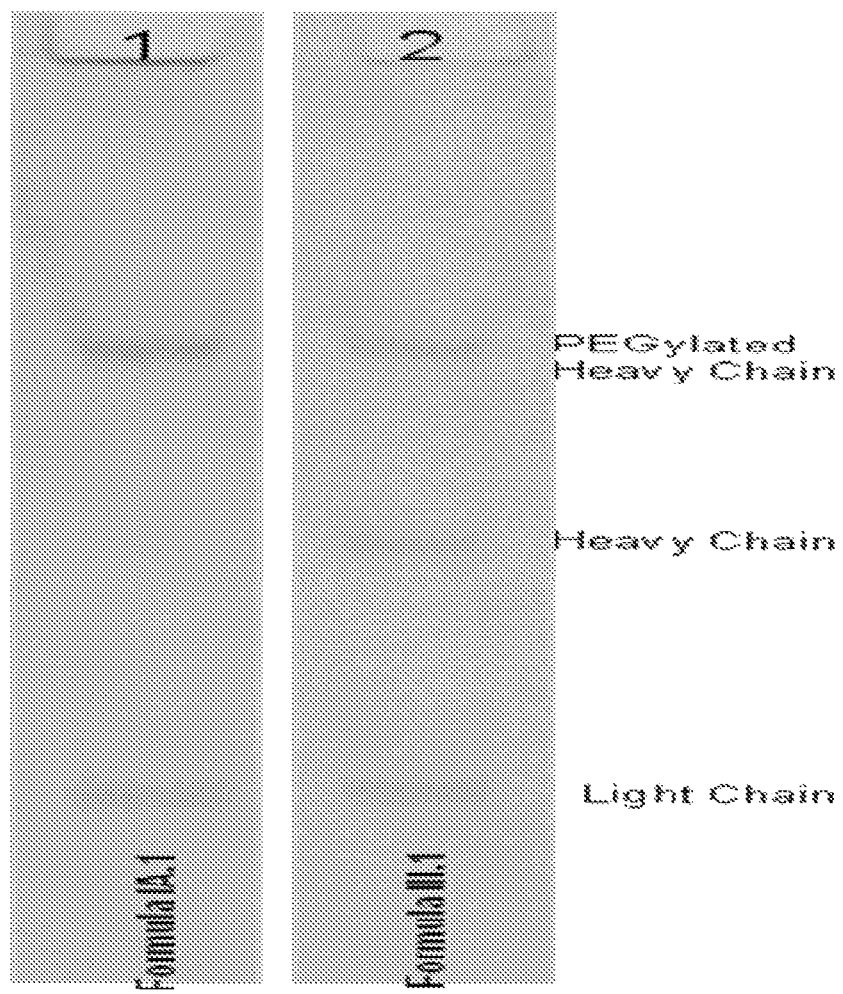

SEQUENCE LISTING

```
<160> NUMBER OF SEQ ID NOS: 17

<210> SEQ ID NO 1
<211> LENGTH: 1365
<212> TYPE: DNA
<213> ORGANISM: Methanosarcina mazei
<220> FEATURE:
<223> OTHER INFORMATION: PylRS Methanosarcina mazei WT nucleotide
      sequence

<400> SEQUENCE: 1
atggataaaa aaccactaaa cactctgata tctgcaaccg ggctctggat gtccaggacc      60
ggaacaattc ataaaataaa acaccacgaa gtctctcgaa gcaaaatcta tattgaaatg     120
gcatgcggag accaccttgt tgtaaacaac tccaggagca gcaggactgc aagagcgctc     180
aggcaccaca aatacaggaa gacctgcaaa cgctgcaggg tttcggatga ggatctcaat     240
aagttcctca caaaggcaaa cgaagaccag acaagcgtaa aagtcaaggt cgtttctgcc     300
cctaccagaa cgaaaaaggc aatgccaaaa tccgttgcga gagccccgaa acctcttgag     360
aatacagaag cggcacaggc tcaaccttct ggatctaaat tttcacctgc gataccggtt     420
tccacccaag agtcagtttc tgtcccggca tctgtttcaa catcaatatc aagcatttct     480
acaggagcaa ctgcatccgc actggtaaaa gggaatacga accccattac atccatgtct     540
gcccctgttc aggcaagtgc ccccgcactt acgaagagcc agactgacag gcttgaagtc     600
ctgttaaacc caaaagatga gatttccctg aattccggca agccttttcag ggagcttgag     660 tccgaattgc tctctcgcag aaaaaaagac ctgcagcaga tctacgcgga agaaaggggag     720 aattatctgg ggaaactcga gcgtgaaatt accaggttct ttgtggacag gggttttctg     780
gaaataaaat ccccgatcct gatccctctt gagtatatcg aaaggatggg cattgataat     840
gataccgaac tttcaaaaca gatcttcagg gttgacaaga acttctgcct gagacccatg     900
cttgctccaa acctttacaa ctacctgcgc aagcttgaca gggccctgcc tgatccaata     960 aaaattttg aaataggccc atgctacaga aaagagtccg acggcaaaga acacctcgaa    1020
gagtttacca tgctgaactt ctgccagatg ggatcggat gcacacggga aaatcttgaa     1080
agcataatta cggacttcct gaaccacctg ggaattgatt tcaagatcgt aggcgattcc    1140
tgcatggtct atggggatac ccttgatgta atgcacgag acctggaact ttcctctgca     1200
gtagtcggac ccataccgct tgaccgggaa tggggtattg ataaaccctg gataggggca    1260 ggttcgggc tcgaacgcct tctaaaggtt aaacacgact ttaaaaatat caagagagct    1320
gcaaggtccg agtcttacta taacgggatt ctaccaacc tgtaa                     1365

<210> SEQ ID NO 2
```

<211> LENGTH: 454
<212> TYPE: PRT
<213> ORGANISM: Methanosarcina mazei
<220> FEATURE:
<223> OTHER INFORMATION: PylRS, Methanosarcina mazei WT amino acid sequence

<400> SEQUENCE: 2

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
```

```
                370             375             380
Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
                435                 440                 445

Gly Ile Ser Thr Asn Leu
    450

<210> SEQ ID NO 3
<211> LENGTH: 1365
<212> TYPE: DNA
<213> ORGANISM: Artificial Sequence
<220> FEATURE:
<223> OTHER INFORMATION: PylRS Methanosarcina mazei Y384F mutant
      nucleotide sequence

<400> SEQUENCE: 3
atggataaaa aaccactaaa cactctgata tctgcaaccg gctctggat gtccaggacc     60 ggaacaattc ataaaataaa acaccacgaa gtctctcgaa gcaaaatcta tattgaaatg    120
gcatgcggag accaccttgt tgtaaacaac tccaggagca gcaggactgc aagagcgctc    180
aggcaccaca atacaggaa gacctgcaaa cgctgcaggg tttcggatga ggatctcaat    240
aagttcctca caaggcaaa cgaagaccag acaagcgtaa agtcaaggt cgtttctgcc    300 cctaccagaa cgaaaaggc aatgccaaaa tccgttgcga gagccccgaa acctcttgag    360
aatacagaag cggcacaggc tcaaccttct ggatctaaat tttcacctgc gataccggtt    420
tccacccaag agtcagtttc tgtcccggca tctgtttcaa catcaatatc aagcatttct    480
acaggagcaa ctgcatccgc actggtaaaa gggaatacga ccccattac atccatgtct    540 gccctgttc aggcaagtgc ccccgcactt acgaagagcc agactgacag gcttgaagtc    600
ctgttaaacc caaagatga gatttccctg aattccggca agcctttcag ggagcttgag    660
tccgaattgc tctctcgcag aaaaaagac ctgcagcaga tctacgcgga agaaagggag    720
aattatctgg ggaaactcga gcgtgaaatt accaggttct tgtggacag gggttttctg    780 gaaataaaat ccccgatcct gatccctctt gagtatatcg aaaggatggg cattgataat    840
gataccgaac tttcaaaaca gatcttcagg gttgacaaga acttctgcct gagacccatg    900
cttgctccaa accttacaa ctacctgcgc aagcttgaca gggccctgcc tgatccaata    960 aaaattttg aaataggccc atgctacaga aaagagtccg acggcaaaga acacctcgaa   1020
gagtttacca tgctgaactt ctgccagatg ggatcgggat gcacacggga aaatcttgaa   1080
agcataatta cggacttcct gaaccacctg ggaattgatt tcaagatcgt aggcgattcc   1140
tgcatggtct ttgggatac ccttgatgta atgcacggag acctgaact ttcctctgca   1200 gtagtcggac ccataccgct tgaccgggaa tggggtattg ataaaccctg gataggggca   1260
ggtttcgggc tcgaacgcct tctaaaggtt aaacacgact taaaaatat caagagagct   1320 gcaaggtccg agtcttacta taacgggatt tctaccaacc tgtaa                  1365

<210> SEQ ID NO 4
<211> LENGTH: 454
<212> TYPE: PRT
<213> ORGANISM: Artificial Sequence
```

<220> FEATURE:
<223> OTHER INFORMATION: PylRS Methanosarcina mazei Y384F mutant amino acid sequence

<400> SEQUENCE: 4

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Phe
    370                 375                 380

Gly Asp Thr Leu Asp Val Met His Gly Asp Leu Glu Leu Ser Ser Ala
```

```
                385                 390                 395                 400
Val Val Gly Pro Ile Pro Leu Asp Arg Glu Trp Gly Ile Asp Lys Pro
                405                 410                 415
Trp Ile Gly Ala Gly Phe Gly Leu Glu Arg Leu Leu Lys Val Lys His
                420                 425                 430
Asp Phe Lys Asn Ile Lys Arg Ala Ala Arg Ser Glu Ser Tyr Tyr Asn
                435                 440                 445
Gly Ile Ser Thr Asn Leu
        450

<210> SEQ ID NO 5
<211> LENGTH: 72
<212> TYPE: DNA
<213> ORGANISM: Methanosarcina mazei
<220> FEATURE:
<223> OTHER INFORMATION: tRNApyl Methanosarcina mazei Go1

<400> SEQUENCE: 5
ggaaacctga tcatgtagat cgaatggact ctaaatccgt tcagccgggt tagattcccg      60
gggtttccgc ca                                                         72

<210> SEQ ID NO 6
<211> LENGTH: 250
<212> TYPE: DNA
<213> ORGANISM: Unknown
<220> FEATURE:
<223> OTHER INFORMATION: U6 snRNA promoter

<400> SEQUENCE: 6
agagggccta tttcccatga ttccttcata tttgcatata cgatacaagg ctgttagaga      60
gataattaga attaatttga ctgtaaacac aaagatatta gtacaaaata cgtgacgtag     120
aaagtaataa tttcttgggt agtttgcagt tttaaaatta tgttttaaaa tggactatca     180
tatgcttacc gtaacttgaa agtatttcga tttcttggct ttatatatct tgtggaaagg     240
acgaaacacc                                                            250

<210> SEQ ID NO 7
<211> LENGTH: 372
<212> TYPE: DNA
<213> ORGANISM: Artificial Sequence
<220> FEATURE:
<223> OTHER INFORMATION: U6-tRNApyl construct

<400> SEQUENCE: 7
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttttaa aattatgttt     180 taaaatggac tatcatatgc ttaccgtaac ttgaaagtat ttcgatttct tggctttata     240
tatcttgtgg aaaggacgaa acaccgaatt ctctagactc gagggaaacc tgatcatgta     300
gatcgaatgg actctaaatc cgttcagccg ggttagattc ccggggtttc cggacaagtg     360 cggttttttgt tt                                                        372

<210> SEQ ID NO 8
<211> LENGTH: 1104
<212> TYPE: DNA
<213> ORGANISM: Unknown
<220> FEATURE:
<223> OTHER INFORMATION: GFP nucleotide sequence
```

<400> SEQUENCE: 8

```
atggcctcca aaggagaaga acttttcact ggagttgtcc caattcttgt tgaattagat      60
ggtgatgtta atgggcacaa attttctgtc agtggagagg gtgaaggtga tgctacatac     120
ggaaagctta cccttaaatt tatttgcact actggaaaac tacctgttcc atggccaaca     180
cttgtcacta ctttctctta tggtgttcaa tgcttttccc gttatccgga tcatatgaaa     240
cggcatgact ttttcaagag tgccatgccc gaaggttatg tacaggaacg cactatatct     300
ttcaaagatg acgggaacta caagacgcgt gctgaagtca agtttgaagg tgatacccct     360
gttaatcgta tcgagttaaa aggtattgat tttaaagaag atggaaacat tctcggacac     420
aaactcgagt acaactataa ctcacacaat gtatacatca cggcagacaa acaaaagaat     480
ggaatcaaag ctaacttcaa aattcgtcac aacattgaag atggatccgt tcaactagca     540
gaccattatc aacaaaatac tccaattggc gatggccctg tcctttacc agacaaccat      600
tacctgtcga cacaatctgc cctttcgaaa gatcccaacg aaaagcgtga ccacatggtc     660
cttcttgagt ttgtaactgc tgctgggatt acacatggca tggatcaggc caagcctttg     720
tctcaagaag aatccaccct cattgaaaga gcaacggcta caatcaacag catccccatc     780
tctgaagact acagcgtcgc cagcgcagct ctctctagcg acggccgcat cttcactggt     840
gtcaatgtat atcattttac tgggggacct tgtgcagaac tcgtggtgct gggcactgct     900
gctgctgcgg cagctggcaa cctgacttgt atcgtcgcga tcggaaatga gaacaggggc     960
atcttgagcc cctgcggacg gtgccgacag gtgcttctcg atctgcatcc tgggatcaaa    1020
gccatagtga aggacagtga tggacagccg acggcagttg ggattcgtga attgctgccc    1080
tctggttatg tgtgggaggg ctaa                                           1104
```

<210> SEQ ID NO 9
<211> LENGTH: 367
<212> TYPE: PRT
<213> ORGANISM: Unknown
<220> FEATURE:
<223> OTHER INFORMATION: GFP amino acid sequence

<400> SEQUENCE: 9

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
```

```
                145                 150                 155                 160
Gly Ile Lys Ala Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Ala Leu Ser
                260                 265                 270

Ser Asp Gly Arg Ile Phe Thr Gly Val Asn Val Tyr His Phe Thr Gly
            275                 280                 285

Gly Pro Cys Ala Glu Leu Val Val Leu Gly Thr Ala Ala Ala Ala Ala
        290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
                340                 345                 350

Val Gly Ile Arg Glu Leu Leu Pro Ser Gly Tyr Val Trp Glu Gly
            355                 360                 365

<210> SEQ ID NO 10
<211> LENGTH: 1104
<212> TYPE: DNA
<213> ORGANISM: Artificial Sequence
<220> FEATURE:
<223> OTHER INFORMATION: GFPY40 nucleotide sequence

<400> SEQUENCE: 10
atggcctcca aaggagaaga acttttcact ggagttgtcc caattcttgt tgaattagat      60
ggtgatgtta atgggcacaa attttctgtc agtggagagg gtgaaggtga tgctacatag     120
ggaaagctta cccttaaatt tatttgcact actggaaaac tacctgttcc atggccaaca     180
cttgtcacta ctttctctta tggtgttcaa tgcttttccc gttatccgga tcatatgaaa     240
cggcatgact ttttcaagag tgccatgccc gaaggttatg tacaggaacg cactatatct     300
ttcaaagatg acgggaacta caagacgcgt gctgaagtca gtttgaagg tgataccctt      360 gttaatcgta tcgagttaaa aggtattgat tttaagaag atggaaacat tctcggacac      420
aaactcgagt acaactataa ctcacacaat gtatacatca cggcagacaa acaaaagaat     480
ggaatcaaag ctaacttcaa aattcgtcac aacattgaag atggatccgt tcaactagca     540
gaccattatc aacaaaatac tccaattggc gatggccctg tccttttacc agacaaccat     600
tacctgtcga cacaatctgc cctttcgaaa gatcccaacg aaaagcgtga ccacatggtc     660
cttcttgagt ttgtaactgc tgctgggatt acacatggca tggatcaggc caagcctttg     720
tctcaagaag aatccaccct cattgaaaga gcaacggcta caatcaacag catccccatc     780
tctgaagact acagcgtcgc cagcgcagct ctctctagcg acggccgcat cttcactggt     840
```

```
gtcaatgtat atcattttac tgggggacct tgtgcagaac tcgtggtgct gggcactgct    900
gctgctgcgg cagctggcaa cctgacttgt atcgtcgcga tcggaaatga aacaggggc     960 atcttgagcc cctgcggacg gtgccgacag gtgcttctcg atctgcatcc tgggatcaaa   1020
gccatagtga aggacagtga tggacagccg acggcagttg ggattcgtga attgctgccc   1080
tctggttatg tgtgggaggg ctaa                                           1104
```

<210> SEQ ID NO 11
<211> LENGTH: 367
<212> TYPE: PRT
<213> ORGANISM: Artificial Sequence
<220> FEATURE:
<223> OTHER INFORMATION: GFPY40 amino acid sequence
<220> FEATURE:
<221> NAME/KEY: MUTAGEN
<222> LOCATION: 40
<223> OTHER INFORMATION: Xaa = unspecified nnAA

<400> SEQUENCE: 11

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Xaa Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Leu Ser
            260                 265                 270

Ser Asp Gly Arg Ile Phe Thr Gly Val Asn Val Tyr His Phe Thr Gly
        275                 280                 285

Gly Pro Cys Ala Glu Leu Val Val Leu Gly Thr Ala Ala Ala Ala Ala
```

290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
                340                 345                 350

Val Gly Ile Arg Glu Leu Leu Pro Ser Gly Tyr Val Trp Glu Gly
            355                 360                 365

<210> SEQ ID NO 12
<211> LENGTH: 1413
<212> TYPE: DNA
<213> ORGANISM: Artificial Sequence
<220> FEATURE:
<223> OTHER INFORMATION: anti-Her2 (4D5) gamma nucleotide sequence

<400> SEQUENCE: 12

```
atggaggctc cgcccagct gctctttctg ctccttctct ggcttcccga cacaaccggt      60
gaggtgcagc tggtggagtc tggcggtggc ttggtacagc cgggcgggtc cctgcgcctc     120
tcctgtgccg cttccggatt caacatcaaa gacacgtata ttcactgggt ccgtcaggca     180
cctggcaagg gtctggagtg ggtgagccgc atttatccta ccaatggtta cactcgctac     240
gccgactctg tgaagggccg cttcaccatc agcgccgaca cgtccaagaa caccctgtat     300
ctgcaaatga acagcctgcg tgccgaggac accgcggtgt attactgcag ccgctgggcc     360
ggtgatggct tttacgcgat ggactactgg ggccagggca ccctggtcac cgtctcgagt     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gcagccccg agaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tga                                 1413
```

<210> SEQ ID NO 13
<211> LENGTH: 470
<212> TYPE: PRT
<213> ORGANISM: Artificial Sequence
<220> FEATURE:
<223> OTHER INFORMATION: anti-Her2 (4D5) gamma amino acid sequence

<400> SEQUENCE: 13

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
```

405                 410                 415
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 14
<211> LENGTH: 1413
<212> TYPE: DNA
<213> ORGANISM: Artificial Sequence
<220> FEATURE:
<223> OTHER INFORMATION: anti-Her2 (4D5) gamma_K274amber nucleotide
      sequence

<400> SEQUENCE: 14

| | | | | | |
|---|---|---|---|---|---|
| atggaggctc | cgcccagct | gctctttctg | ctccttctct | ggcttcccga | cacaaccggt | 60 |
| gaggtgcagc | tggtggagtc | tggcggtggc | ttggtacagc | cgggcgggtc | cctgcgcctc | 120 |
| tcctgtgccg | cttccggatt | caacatcaaa | gacacgtata | ttcactgggt | ccgtcaggca | 180 |
| cctggcaagg | gtctggagtg | ggtgagccgc | atttatccta | ccaatggtta | cactcgctac | 240 |
| gccgactctg | tgaagggccg | cttcaccatc | agcgccgaca | cgtccaagaa | caccctgtat | 300 |
| ctgcaaatga | acagcctgcg | tgccgaggac | accgcggtgt | attactgcag | ccgctggggc | 360 |
| ggtgatggct | tttacgcgat | ggactactgg | ggccagggca | ccctggtcac | cgtctcgagt | 420 |
| gctagcacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagaa | agttgagccc | 720 |
| aaatcttgtg | acaaaactca | cacatgccca | ccgtgcccag | cacctgaact | cctgggggga | 780 |
| ccgtcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcta | gttcaactgg | 900 |
| tacgtggacg | gcgtggaggt | gcataatgcc | aagacaaagc | cgcgggagga | gcagtacaac | 960 |
| agcacgtacc | gtgtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | gcagccccg | agaaccacag | gtgtacaccc | tgcccccatc | ccgggaggag | 1140 |
| atgaccaaga | accaggtcag | cctgacctgc | ctggtcaaag | gcttctatcc | cagcgacatc | 1200 |
| gccgtggagt | gggagagcaa | tgggcagccg | gagaacaact | acaagaccac | gcctcccgtg | 1260 |
| ctggactccg | acggctcctt | cttcctctac | agcaagctca | ccgtggacaa | gagcaggtgg | 1320 |
| cagcagggga | acgtcttctc | atgctccgtg | atgcatgagg | ctctgcacaa | ccactacacg | 1380 |
| cagaagagcc | tctccctgtc | tccgggtaaa | tga | | | 1413 |

<210> SEQ ID NO 15
<211> LENGTH: 470
<212> TYPE: PRT
<213> ORGANISM: Artificial Sequence
<220> FEATURE:

<223> OTHER INFORMATION: anti-Her2 (4D5) gamma_K274amber amino acid
      sequence
<220> FEATURE:
<221> NAME/KEY: MUTAGEN
<222> LOCATION: 297
<223> OTHER INFORMATION: Xaa = pyrrolysine analogue of formula III.1 or
      1A.1

<400> SEQUENCE: 15

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Xaa Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365
```

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 16
<211> LENGTH: 705
<212> TYPE: DNA
<213> ORGANISM: Artificial Sequence
<220> FEATURE:
<223> OTHER INFORMATION: anti-Her2 (4D5) Kappa nucleotide sequence

<400> SEQUENCE: 16
atggaggctc cgcccagct gctctttctg ctccttctct ggcttcccga cacaaccggt      60
gacatccaga tgacccagtc tccatcctcc ctgtctgcat ctgtgggaga ccgtgtcaca     120
atcacttgcc gtgctagcca ggatgtgaat acagcggtgg cctggtatca gcagaaacct     180
ggcaaagccc ctaagctcct gatctattct gcatcctttt tgtacagcgg cgtgccgagc     240
cgcttcagcg gcagccgttc tggtaccgat ttcactctca ccatcagctc tctgcaaccg     300
gaagattttg caacttacta ctgtcaacag cactaccaca ctcctccgac gttcggccaa     360
gggaccaagg tggaaatcga acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagttcgc ccgtcacaaa gagcttcaac agggagagt gttaa                      705

<210> SEQ ID NO 17
<211> LENGTH: 234
<212> TYPE: PRT
<213> ORGANISM: Artificial Sequence
<220> FEATURE:
<223> OTHER INFORMATION: anti-Her2 (4D5) Kappa amino acid sequence

<400> SEQUENCE: 17

Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

```
Arg Phe Ser Gly Ser Arg Ser Gly Thr Asp Phe Thr Leu Thr Ile Ser
            85              90                  95
Ser Leu Gln Pro Glu Asp Phe Ala Thr Tyr Tyr Cys Gln Gln His Tyr
            100             105             110
Thr Thr Pro Pro Thr Phe Gly Gln Gly Thr Lys Val Glu Ile Glu Arg
            115             120             125
Thr Val Ala Ala Pro Ser Val Phe Ile Phe Pro Pro Ser Asp Glu Gln
    130             135             140
Leu Lys Ser Gly Thr Ala Ser Val Val Cys Leu Leu Asn Asn Phe Tyr
145             150             155             160
Pro Arg Glu Ala Lys Val Gln Trp Lys Val Asp Asn Ala Leu Gln Ser
            165             170             175
Gly Asn Ser Gln Glu Ser Val Thr Glu Gln Asp Ser Lys Asp Ser Thr
            180             185             190
Tyr Ser Leu Ser Ser Thr Leu Thr Leu Ser Lys Ala Asp Tyr Glu Lys
        195             200             205
His Lys Val Tyr Ala Cys Glu Val Thr His Gln Gly Leu Ser Ser Pro
    210             215             220
Val Thr Lys Ser Phe Asn Arg Gly Glu Cys
225             230
```

AMINO ACID DERIVATIVES

CROSS-REFERENCE TO RELATED APPLICATIONS

This application is a U.S. National Stage Application of International Application No. PCT/IB2014/002505, filed on Aug. 4, 2014, said International Application No. PCT/IB2014/002505 claims benefit under 35 U.S.C. § 119(e) of the U.S. Provisional Application No. 61/862,497, filed Aug. 5, 2013. Each of the above listed applications is incorporated by reference herein in its entirety for all purposes.

REFERENCE TO THE SEQUENCE LISTING

This application incorporates by reference a Sequence Listing submitted with this application as text file entitled ALLO-280WO1_sequence_listing, created on Dec. 3, 2015, and having a size of 37.0 kilobytes.

The invention relates to amino acid derivatives for use in bioconjugation processes.

INTRODUCTION

Pyrrolysine is a natural amino acid, the only one that is authentically specified by an amber codon. It uses a 21st aminoacyl-tRNA synthetase (PylRS), naturally evolved to be orthogonal to all other amino acids and tRNAs. Blight et al., 2004 showed that PylRS and its counterpart tRNA (tRNApyl) can incorporate pyrrolysine at amber codons in *E. coli*. They also showed that the wt PylRS is naturally promiscuous and can incorporate analogs of lysine.

Yokoyama et al. (EP1911840) demonstrated that the PylRS/tRNApyl system is orthogonal in eukaryotic cells and showed the incorporation of several non natural amino acids (nnAAs) into a target proteins encoded by amber codons in bacterial cells. These authors also identified key amino acid residues in pylRS that form the amino acid binding pocket and function in selecting pyrrolysine over other canonical amino acids. Mutations at this site generated mutants able to recognize and aminoacylate the tRNApyl with AzZ-lys (Yanagisawa, 2008).

This orthogonality extends to bacteria and eukaryotic cells.

PylRS is a naturally promiscuous synthetase that has naturally evolved to exclude lysine, but will incorporate lysine analogs without mutation, including azides, alkynes and alkenes (Yanagisawa et al., 2008; Neumann et al., 2008; Mukai et al., 2008; Nguyen et al., 2009). The basis of this specificity is dependent on hydrophobic interactions between amino acid residues of the pylRS binding pocket with the pyrrole ring of pyrrolysine that stabilizes and correctly positions the amino acid in the active site of the synthetase (Kavran et al., 2007). This RS/tRNA pair has been introduced via transient transfection into bacterial, yeast and mammalian cells and shown to be effective for incorporation of a number of non-natural amino acids into target proteins.

For instance, EP 1911840 demonstrates incorporation of N-ε-boc-Lysine into a target protein in *E. coli* cells.

Pyrrolysine analogs, defined as amino acid derivatives recognized by either native or genetically evolved PylRS and incorporated into proteins at amber codon sites, have been disclosed in the past few years and reviewed, for instance, by Fekner et al. (Fekner, Li & Chan, 2010) and Liu et al. Analogs bearing functional groups or post translational modifications have been site-specifically incorporated into proteins using pylRS-tRNApyl systems. Several studies, see e.g., Yanagisawa et al., focused on mutations within the PylRS enzyme in order to accommodate analogs in which the N6 substituent was an aromatic ring within the binding pocket pyrrolysine. Others, for instance Nguyen et al. (also in WO2010/139948), and Li et al. (also in WO2011/044255) focused on identification of pyrrolysine analogs which do not carry a bulky N6 substituent, with the result of obtaining simpler analogs which would be simple to synthesize and interact with native pylRS/tRNApyl pairs. Furthermore, Chin et al. developed two analogs with terminal alkyne and azide groups, amenable to use for protein labeling via Copper catalyzed click chemistry (CUAAC).

There remains a need to develop further pyrrolysine analogs. Whilst pyrrolysine analogs made thus far have been restricted to those evolved from a lysine backbone, the present inventors have generated pyrrolysine analogs successfully incorporated into proteins with native pylRS/tRNApyl pairs starting from a variety of amino acid structures.

SUMMARY OF THE INVENTION

According to the invention there are provided pyrrolysine analogues of formulae I to VIII as described herein.

There is also provided a mutant protein containing as non-natural amino acid one or more (e.g., one) pyrrolysine analogues of formulae I to VIII as described herein.

There is also provided a mutant protein as aforesaid which is conjugated via the one or more (e.g., one) non-natural amino acids to one or more (e.g., one) moieties selected from proteins, cytotoxic agents, drugs and polymers.

There is also provided use of a pyrrolysine analogue as aforesaid in the manufacture of a mutant protein containing one or more non-natural amino acids.

Amino acid analogs described in the present invention are new and useful and have the merit of being straightforward to prepare, in being readily incorporated into proteins (typically without loss of bioactivity when used appropriately) and in providing useful means for bioconjugation.

BRIEF DESCRIPTION OF THE FIGURES

FIG. 1: PEGylation of azide containing monoclonal antibodies. Lane 1: Antibody with Formula IA.1 analog incorporated into heavy chain and subjected to PEGylation conditions; Lane 2: Antibody with Formula III.1 analog incorporated into heavy chain and subjected to PEGylation conditions.

BRIEF DESCRIPTION OF THE SEQUENCES OF THE SEQUENCE LISTING

SEQ ID No 1: PylRS *Methanosarcina mazei* WI nucleotide sequence
SEQ ID No 2: PylRS *Methanosarcina mazei* WT amino acid sequence
SEQ ID No 3: PylRS *Methanosarcina mazei*, Y384F mutant nucleotide sequence
SEQ ID No 4: PylRS *Methanosarcina mazei*, Y384F mutant amino acid sequence
SEQ ID No 5: tRNApyl *Methanosarcina mazei* Go1
SEQ ID No 6: U6 snRNA Promoter
SEQ ID No 7: U6-tRNApyl construct
SEQ ID No 8: GFP nucleotide sequence
SEQ ID No 9: GP amino acid sequence
SEQ ID No 10: GFPY40 nucleotide sequence SEQ ID No 11: GFPY40 amino add sequence
SEQ ID No 12: anti-Her2 (4D5) gamma nucleotide sequence
SEQ ID No 13: anti-Her2 (4D5) gamma amino acid sequence
SEQ ID No 14: anti-Her2 (4D5) gamma_K274amber nucleotide sequence
SEQ ID No 15: anti-Her2 (4D5) gamma_K274amber amino add sequence
SEQ ID No 16: anti-Her2 (4D5)Kappa nucleotide sequence
SEQ ID No 17: anti-Her2 (4D5)Kappa amino add sequence

DETAILED DESCRIPTION OF THE INVENTION

Definitions

The term "amide" refers to a —C(=O)—NH— linkage.

The term "carbamate" refers to a —O—C(=O)—NH— linkage.

The term "ester" refers to a —C—C(=O)—O—C linkage.

The term "alkyl" refers to an aliphatic linkage or substituent, typically containing 1-6 e.g., 1-4 carbon atoms and can be straight chain or branched. Examples include methyl, ethyl, n-propyl, i-propyl, n-butyl and t-butyl.

The term "alkoxy" refers to the group —O-alkyl.

The term "alkenyl", "alkene" or "olefin" refers to an aliphatic linkage or substituent, typically containing 2-6 e.g., 2-4 carbon atoms and can be straight chain or branched and which is unsaturated in respect of containing at least one C=C moiety. Examples include ethenyl, propen-1-yl, propen-2-yl, and 2-methyl-propen-2-yl. An alkenyl group may be optionally substituted e.g., by one or more (e.g., 1) substituents such as halogen (e.g., Cl) or an ether group (e.g., —O—C$_{1-6}$alkyl) although suitably it is not substituted.

The term "alkynyl" or "alkyne" refers to an aliphatic linkage or substituent, typically containing 2-6 e.g., 2-4 carbon atoms and can be straight chain or branched and which is unsaturated in respect of containing at least one C≡C moiety. Examples include —C≡CH and —C≡C—CH$_3$. An alkynyl group may be optionally substituted e.g., by one or more (e.g., 1) substituents such as halogen (e.g., Cl) or an ether group (e.g., —O—C$_{1-6}$alkyl) although suitably it is not substituted.

The term "cycloalkyl" refers to an alicyclic and unsaturated compound typically containing 3 to 8 cyclic carbon atoms. Cycloalkyl groups may containing branching. The total number of carbon atoms will typically be 3 to 10. Exemplary groups include cyclopropyl, cyclobutyl, cyclopentyl, 3-methyl-cyclopropyl and cyclohexyl.

The term "cycloalkenyl" refers to an alicyclic compound typically containing 5 to 8 cyclic carbon atoms and containing at last one C=C moiety. Cycloalkenyl groups may containing branching.

The total number of carbon atoms will typically be 5 to 10. Exemplary groups include cyclopentenyl, 3-methyl-cyclopropenyl and cyclohexenyl.

The term "heterocyclyl" refers to a cycloalkyl or cycloalkenyl moiety in which the ring contains one or more (e.g., one, two or three, such as one or two, especially one) heteroatoms selected from O, N and S. Examples include azetidine, pyrrolidine, piperidine, piperazine, N-methylpiperazine, morpholine and thiomorpholine.

The term "aryl" refers to an aromatic ring structure that can be part of a linkage or part of a substituent. Aryl moieties may contain one ring (e.g., phenyl) or two rings (e.g., naphthyl). Aryl groups may be substituted e.g., by one or more (e.g., one or two, such as one) substituents selected from alkyl, alkenyl, alkynyl, fluoroalkyl, halogen, alkoxy, nitro and cyano. An exemplary aryl is phenyl.

The term "heteroaryl" refers to a heteroaromatic ring structure that can be part of a linkage or part of a substituent. The heteroaromatic ring may contain 1-4 (more usually 1-3 e.g., one or two) heteroatoms selected from O, N and S. Heteroaryl moieties may contain one ring or two rings. Example groups containing one 6 membered ring include pyridine and pyrimidine. Example groups containing one 5 membered ring include pyrrole, furan, thiophene, oxazole, thiazole, diazole, thiadiazole and tetrazole. Heteroaryl moieties that contain two rings may contain heteroatoms in one or both rings. Examples include quinoline and isoquinoline. Heteroaryl groups may be substituted e.g., by one or more (e.g., one or two, such as one) substituents selected from alkyl, alkenyl, alkynyl, fluoroalkyl, halogen, alkoxy, nitro and cyano.

The term "aromatic halide" refers to an aromatic ring (typically phenyl) which is substituted by at least one (e.g., one) halo group such as fluorine, chloride, bromide or iodine. Said aromatic ring may contain further substituents e.g., those mentioned for aryl.

The term "azide" and "azido" refers to a N=N(+)=N(−) functional group.

The term "cycloalkyne" refers to a cyclic arrangement of carbon atoms (typically 6-9 membered, especially 8-9 membered) which includes a carbon-carbon triple bond captured in the ring structure. Examples include cyclooctyne and cyclononyne. A further example is benzyne. Cycloalkyne groups may containing branching. The total number of carbon atoms will typically be 6 to 12 e.g., 6 to 10.

The term "ketone" refers to a C—C(=O)—C linkage.

The term "pyrrolysine analog" means an amino acid derivative recognized by either native or genetically evolved PylRS and incorporated into proteins at an amber codon site.

The expression "the side chain of one of the 20 natural amino acids" refers to the group R in the formula HOOC—CHR—NH$_2$ relating to the 20 natural amino acids known by their single letter codes A, C, D, E, F, G, H, I, K, L, M, N, P, Q, R, S, T, V, W and Y. Either L or D stereochemistry (or a mixture thereof) is intended, although L stereochemistry is preferred.

The present invention discloses pyrrolysine analogs.

Some pyrrolysine analogs of the present invention have the structure of Formula I:

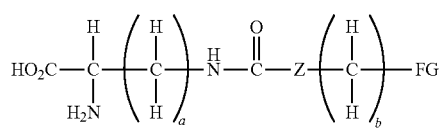

wherein
Z=bond, CH$_2$, CH—NH$_2$, CH—OH, NH, O, S or CH—NH$_2$;
a is an integer 3-7;
b is 0 or an integer 1-7; and
FG=azide, alkene, alkyne, ketone, ester, aryl or cycloalkyne.

Certain compounds of Formula (I) are known.

Thus, compounds of Formula (I) wherein a represents 4, Z represents O and —(CH$_2$)$_b$-FG represents —CH$_2$—C≡CH, —CH$_2$CH$_2$—N$_3$, —CH$_2$—CH=CH$_2$ and —CH$_2$-Ph are disclosed in WO2012/032181. Further compounds of Formula (I) wherein a represents 4, Z represents O and —(CH$_2$)$_b$-FG represents —CH$_2$CH$_2$CH$_2$—C(=O)CH$_3$ and —CH$_2$CH$_2$CH$_2$—CH=CH$_2$ are disclosed in WO2010/139948.

Compounds of Formula (I) wherein a represents 4, Z represents a bond, b represents 0 and —(CH$_2$)$_b$-FG represents —C(=O)Bn and —C(=O)Me are disclosed in WO2012/032181. Further a compound of Formula (I) wherein a represents 4, Z represents a bond and —(CH$_2$)$_b$-FG represents —CH$_2$CH$_2$—C≡CH is disclosed in WO2010/139948.

In an embodiment of the present invention, a compound of Formula I has a=4, resulting in compounds of general Formula IA:

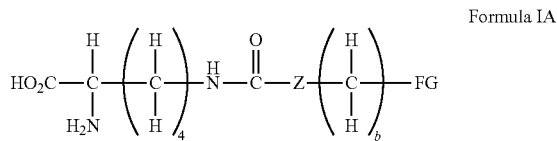

Formula IA

In an alternative embodiment of the present invention, a=3, resulting in compounds of general Formula IB:

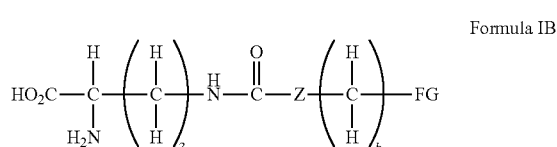

Formula IB

In an embodiment of Formulae I, IA and IB, Z is bond, for example, Z is bond, b is 0 and FG is C(=O)-aryl or C(=O)-alkyl.

In an embodiment of Formulae I, IA and IB, Z is CH$_2$, CH—NH$_2$, CH—OH, NH, O, S or CH—NH$_2$. For example, Z may represent O. Alternatively Z may represent NH. Alternatively Z may represent CH$_2$, CH—NH$_2$, CH—OH, S or CH—NH$_2$.

In an embodiment, b is 1-4.

In an embodiment, FG is azide.

In an embodiment, FG is alkyne (e.g., ethylnyl) or cycloalkyne.

In an embodiment, FG is alkene e.g., ethenyl.

In formulae I, IA and IB, when FG represents aryl, an example is aromatic halide e.g., 4-halo phenyl such as 4-iodo phenyl.

Exemplary compounds of Formula IA are the following:
(2S)-2-amino-6-{[(2-azidoethoxy)carbonyl]amino}hexanoic acid

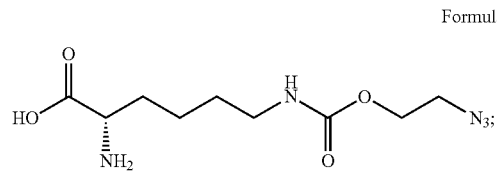

Formula IA.1

(2S)-2-amino-6-{[(prop-2-yn-1-yloxy)carbonyl]amino}hexanoic acid

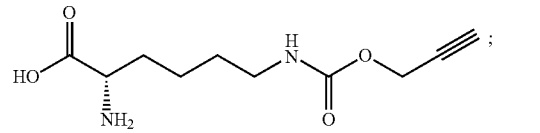

Formula IA.2

(2S)-2-amino-6-{[(prop-2-en-1-yloxy)carbonyl]amino}hexanoic acid

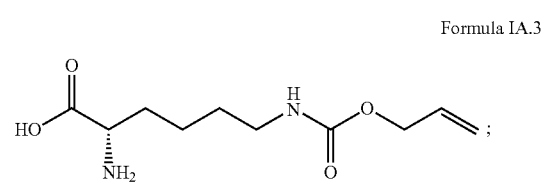 [SMILES: C=CCOC(=O)NCCCC[C@H](N)C(=O)O]

Formula IA.3

(2S)-2-amino-6-{[(2-azidoethyl)carbamoyl]amino}hexanoic acid

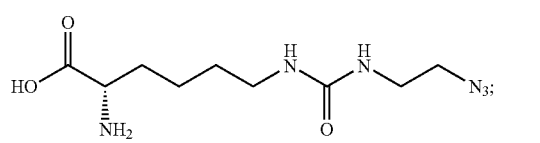

Formula IA.4

(2S)-2-amino-6-{[(prop-2-en-1-yl)carbamoyl]amino}hexanoic acid

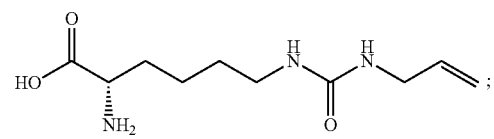

Formula IA.5

(2S)-2-amino-6-{[(3-azidopropoxy)carbonyl]amino}hexanoic acid

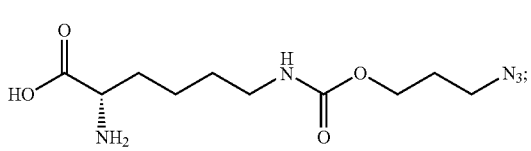

Formula IA.6

(2S)-2-amino-6-[(2S)-2-amino-4-azidobutanamido]
hexanoic acid

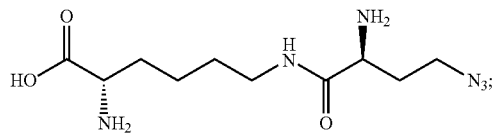

Formula IA.7

(2S)-2-amino-6-({[(4-iodophenyl)methoxy]
carbonyl}amino)hexanoic acid

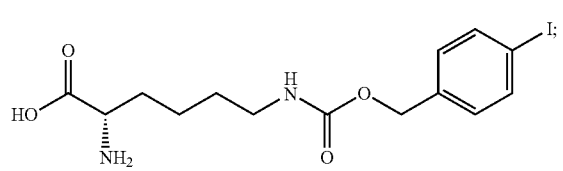

Formula IA.8 and
(2S)-2-amino-6-(4-azidobutanamido)hexanoic acid

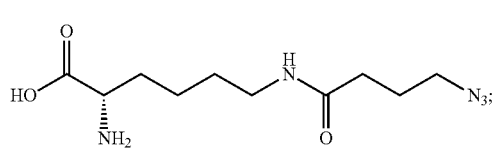

Formula IA.9

The following compounds are examples of compounds of Formula IB:

(2S)-2-amino-5-{[(2-azidoethoxy)carbonyl]
amino}pentanoic acid

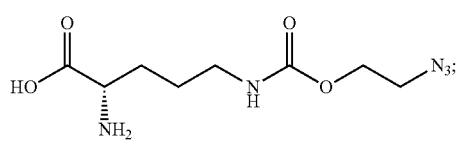

Formula IB.1

(2S)-2-amino-5-{[(prop-2-yn-1-yloxy)carbonyl]
amino}pentanoic acid

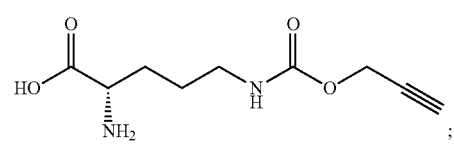

Formula IB.2 and
(2S)-2-amino-5-{[(prop-2-en-1-yloxy)carbonyl]
amino}pentanoic acid

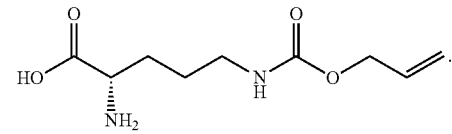

Formula IB.3

Alternative pyrrolysine analogs of the present invention have the structure of Formula II:

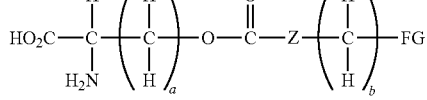

Formula II wherein
Z=$CH_2$, CH—$NH_2$, CH—OH, NH, O or S;
FG=azide, alkene, alkyne, ketone, ester, aryl or cycloalkyne;
a=an integer 3 or 5-7; and
b=an integer 1-4.

In an embodiment, FG is azide. In an embodiment, FG is alkyne e.g., ethynyl or cycloalkyne. In an embodiment, FG is alkene e.g., ethenyl. In an embodiment, Z represents NH. In an embodiment b represents 1 or 2. In an embodiment, $Z(CH_2)_b FG$ represents $NH(CH_2)_2 N_3$ or $NHCH_2 C\equiv CH$.

In formula II, when FG represents aryl, an example is aromatic halide e.g., 4-halo phenyl such as 4-iodo phenyl.

Moiety $Z(CH_2)_b FG$ may, for example, represent CO-aryl e.g., CO-phenyl or —COalkyl e.g., —COMe.

Further pyrrolysine analogs of the present invention have the structure of Formula III:

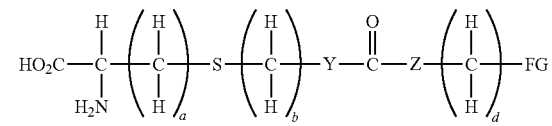

Formula III wherein
Y=$CH_2$, NH, O or S;
Z=$CH_2$, CH—$NH_2$, CH—OH, NH, O or S;
FG=azide, alkene, alkyne, ketone, ester, aryl or cycloalkyne;
a=an integer 1-7;
b=an integer 1-7 save that when Z is NH, O or S then b is an integer 2-7;
provided that a+b is in the range 2-8;
and
d=an integer 1-4.

In an embodiment, a+b is in the range 3-6 e.g., 3-4.
In an embodiment a is 1.
In an embodiment b is 2. In another embodiment b is 3.
In an embodiment, FG is azide.
In an embodiment, FG is alkyne (e.g., ethylnyl) or cycloalkyne.

In an embodiment, FG is alkene e.g., ethenyl.

In formula III, when FG represents aryl, an example is aromatic halide e.g., 4-halo phenyl such as 4-iodo phenyl.

Exemplary compounds of Formula III are:

(2S)-2-amino-3-[(2-{[(2-azidoethoxy)carbonyl]amino}ethyl)sulfanyl]propanoic acid Formula III.1

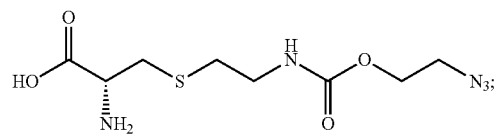

(2S)-2-amino-3-[(2-{[(prop-2-yn-1-yloxy)carbonyl]amino}ethyl)sulfanyl]propanoic acid Formula III.2

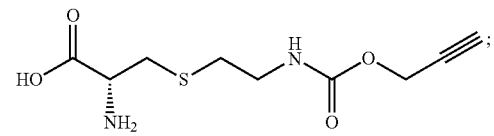

(2S)-2-amino-3-[(2-{[(prop-2-en-1-yloxy)carbonyl]amino}ethyl)sulfanyl]propanoic acid Formula III.3

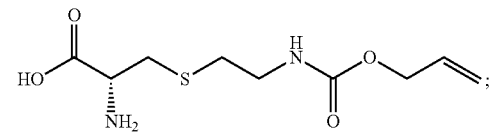

(2S)-2-amino-3-[(2-{[(2-azidoethyl)carbamoyl]amino}ethyl)sulfanyl]propanoic acid Formula III.4

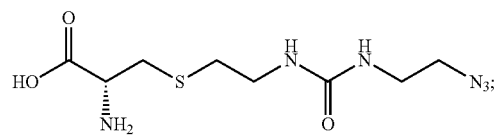

(2S)-2-amino-3-[(2-{[(prop-2-yn-1-yl)carbamoyl]amino}ethyl)sulfanyl]propanoic acid Formula III.5

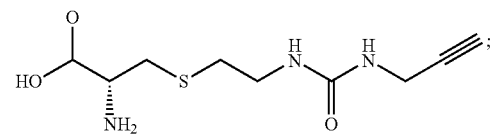

(2S)-2-amino-3-[(2-{[(prop-2-en-1-yl)carbamoyl]amino}ethyl)sulfanyl]propanoic acid Formula III.6

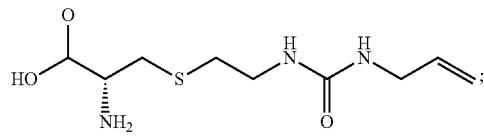

(2S)-2-amino-3-[(2-{[(2-azidoethyl)carbamoyl]oxy}ethyl)sulfanyl]propanoic acid

Formula III.7

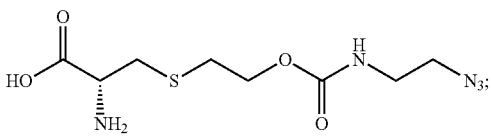

(2S)-2-amino-3-[(2-{[(prop-2-yn-1-yl)carbamoyl]oxy}ethyl)sulfanyl]propanoic acid Formula III.8

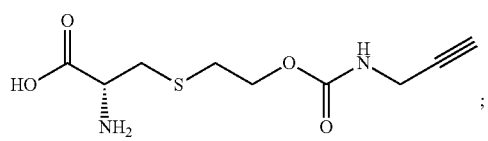

(2S)-2-amino-3-[(2-{[(prop-2-en-1-yl)carbamoyl]oxy}ethyl)sulfanyl]propanoic acid Formula III.9

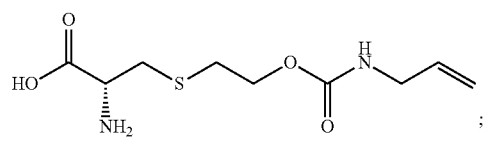

(2S)-2-amino-3-({3-[(2-azidoethyl)carbamoyl]propyl}sulfanyl)propanoic acid

Formula III.10

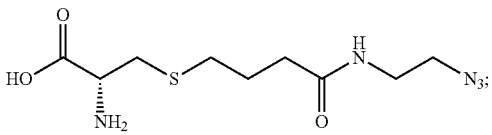

(2S)-2-amino-3-({3-[(prop-2-yn-1-yl)carbamoyl]
propyl}sulfanyl)propanoic acid

Formula III.11

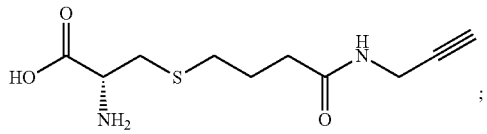

(2S)-2-amino-3-({3-[(prop-2-en-1-yl)carbamoyl]
propyl}sulfanyl)propanoic acid

Formula III.12

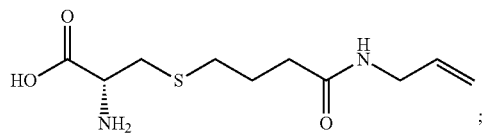

and
(2S)-2-amino-3-({3-[(2-azidoethyl)carbamoyl]
propyl}sulfanyl)propanoic acid

Formula III.13

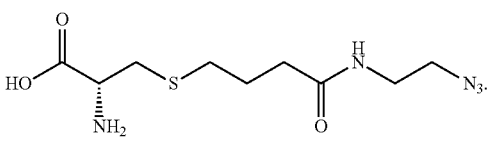

Still further pyrrolysine analogs have the structure of Formula IV:

Formula IV

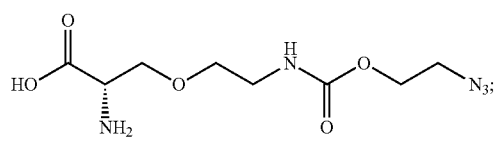

wherein
Y=$CH_2$, NH, O or S;
Z=$CH_2$, CH—$NH_2$, CH—OH, NH, O or S;
FG=azide, alkene, alkyne, ketone, ester, aryl or cycloalkyne;
a=an integer 1-7;
b=an integer 1-7 save that when Z is NH, O or S then b is an integer 2-7;
provided that a+b is in the range 2-8;
and d=an integer 1-4.

In an embodiment, a+b is in the range 3-6 e.g., 3-4.
In an embodiment, a is 1.
In an embodiment, b is 2. In another embodiment b is 3.
In an embodiment, Y is NH and Z is O. In an embodiment, Y is NH and Z is NH. In an embodiment, Y is O and Z is O. In an embodiment, Y is $CH_2$ and Z is NH.
In an embodiment, FG is azide.
In an embodiment, FG is alkyne (e.g., ethylnyl) or cycloalkyne.

In an embodiment, FG is alkene e.g., ethenyl.
In formula IV, when FG represents aryl, an example is aromatic halide e.g., 4-halo phenyl such as 4-iodo phenyl.
More generally, compounds of Formula III and IV are referred to as compounds of formula X:

Formula X

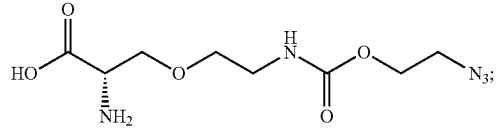

wherein X represents O or S and all other variables are as defined for compounds of formula III or IV.

Exemplary compounds of Formula IV are as follows:
(2S)-2-amino-3-(2-{[(2-azidoethoxy)carbonyl]
amino}ethoxy)propanoic acid Formula IV.1

(2S)-2-amino-3-(2-{[(prop-2-yn-1-yloxy)carbonyl]
amino}ethoxy)propanoic acid

Formula IV.2

(2S)-2-amino-3-(2-{[(prop-2-en-1-yloxy)carbonyl]
amino}ethoxy)propanoic acid

Formula IV.3

(2S)-2-amino-3-(2-{[(2-azidoethyl)carbamoyl]
amino}ethoxy)propanoic acid

Formula IV.4

(2S)-2-amino-3-(2-{[(prop-2-yn-1-yl)carbamoyl]amino}ethoxy)propanoic acid

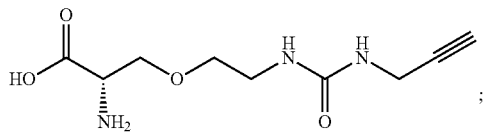

Formula IV.5

(2S)-2-amino-3-(2-{[(prop-2-en-1-yl)carbamoyl]amino}ethoxy)propanoic acid

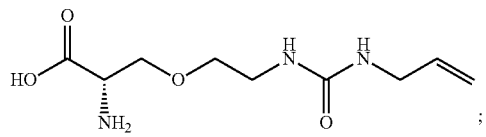

Formula IV.6

(2S)-2-amino-3-(2-{[(2-azidoethyl)carbamoyl]oxy}ethoxy)propanoic acid

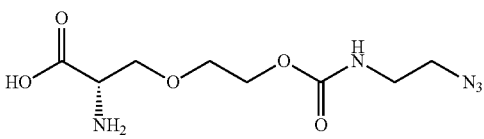

Formula IV.7

(2S)-2-amino-3-(2-{[(prop-2-yn-1-yl)carbamoyl]oxy}ethoxy)propanoic acid

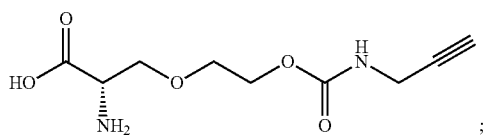

Formula IV.8

(2S)-2-amino-3-(2-{[(prop-2-en-1-yl)carbamoyl]oxy}ethoxy)propanoic acid

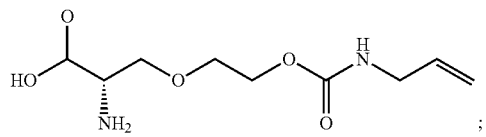

Formula IV.9

(2S)-2-amino-3-{3-[(2-azidoethyl)carbamoyl]propoxy}propanoic acid

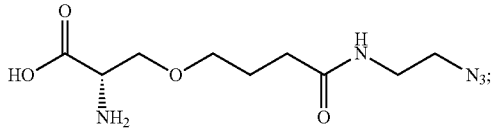

Formula IV.10

(2S)-2-amino-3-{3-[(prop-2-yn-1-yl)carbamoyl]propoxy}propanoic acid

Formula IV.11 and (2S)-2-amino-3-{3-[(prop-2-en-1-yl)carbamoyl]propoxy}propanoic acid

Formula IV.12

Additional pyrrolysine analogs have the structure of Formula V:

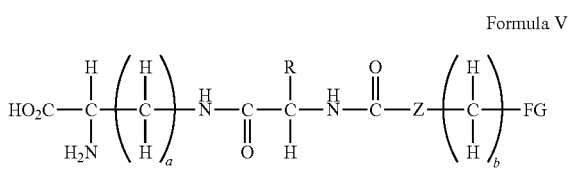

Formula V wherein

R=the side chain of one of the 20 natural amino acids;

Z=$CH_2$, $CH-NH_2$, $CH-OH$, NH, O or S;

FG=azide, alkene, alkyne, ketone, ester, aryl or cycloalkyne;

a=1; and b=an integer 1 to 4.

In an embodiment, Z is O.

In an embodiment, FG is azide.

In an embodiment, FG is alkyne (e.g., ethylnyl) or cycloalkyne.

In an embodiment, FG is alkene e.g., ethenyl.

In formula V, when FG represents aryl, an example is aromatic halide e.g., 4-halo phenyl such as 4-iodo phenyl.

Exemplary compounds of Formula V are as follows:
(2S)-2-amino-3-(2-{[(2-azidoethoxy)carbonyl]
amino}acetamido)propanoic acid

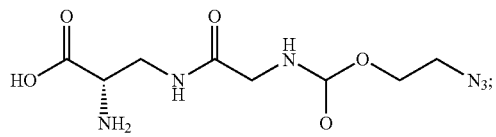

Formula V.1

(2S)-2-amino-3-(2-{[(prop-2-yn-1-yloxy)carbonyl]
amino}acetamido)propanoic acid

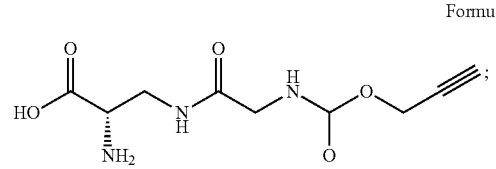

Formula V.2 and
(2S)-2-amino-3-(2-{[(prop-2-en-1-yloxy)carbonyl]
amino}acetamido)propanoic acid

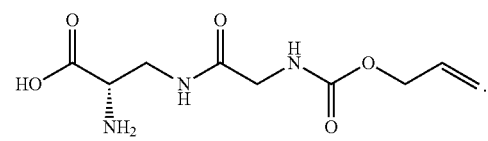

Formula V.3

Additional pyrrolysine analogs have structures of Formula VI:

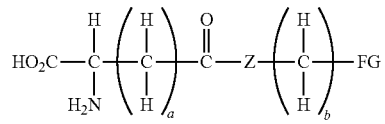

Formula VI wherein
Z=CH$_2$, CH—NH$_2$, CH—OH, NH, O and S;
FG=azide, alkene, alkyne, ketone, ester, aryl and cycloalkyne;
a=4 or 5; and
b=an integer 1 to 4;

In an embodiment, Z is NH.
In an embodiment, a is 5.
In an embodiment, FG is azide.
In an embodiment, FG is alkyne (e.g., ethylnyl) or cycloalkyne.
In an embodiment, FG is alkene e.g., ethenyl.
In Formula VI, when FG represents aryl, an example is aromatic halide e.g., 4-halo phenyl such as 4-iodo phenyl.

The following are exemplary compounds of Formula VI:
(2S)-2-amino-7-[(2-azidoethyl)carbamoyl]heptanoic acid

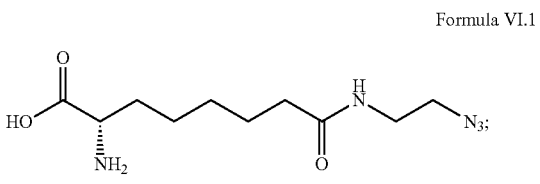 [SMILES: [N-]=[N+]=NCCNC(=O)CCCCC[C@H](N)C(=O)O]

Formula VI.1

(2S)-2-amino-7-[(prop-2-yn-1-yl)carbamoyl]heptanoic acid

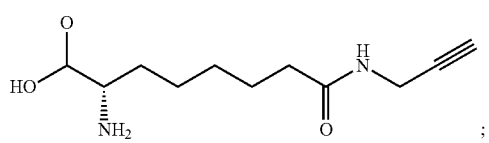

Formula VI.2

(2S)-2-amino-7-[(prop-2-en-1-yl)carbamoyl]heptanoic acid

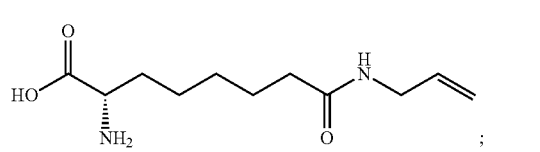

Formula VI.3

Alternative pyrrolysine analogs have structure of Formula VII:

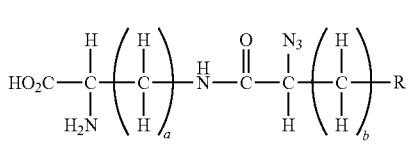

Formula VII wherein
R=alkyl, alkenyl, cycloalkyl, aryl, heteroaryl or heterocyclyl;
a=an integer 1 to 7; and
b=an integer 1 to 3.

In some preferred embodiments, a=4.
A preferred compound of Formula VII is (2S)-2-amino-6-(2-azidopentanamido)hexanoic acid

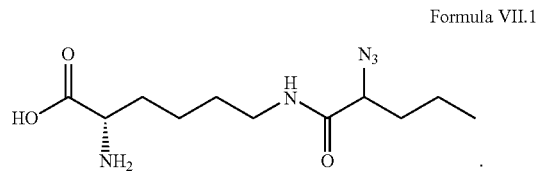 [SMILES: CCCC(N=[N+]=[N-])C(=O)NCCCC[C@H](N)C(=O)O]

Formula VII.1

Alternative pyrrolysine analogs have structure of Formula (VIII):

Formula VIII wherein
Z=CH$_2$, CH—NH$_2$, CH—OH, NH, O or S;
R$_1$=H, alkyl, alkenyl, cycloalkyl, cycloalkenyl, aryl, heteroaryl or heterocyclyl;
R$_2$=alkyl, alkenyl, cycloalkyl, cycloalkenyl, aryl, heteroaryl or heterocyclyl;
R$_3$=H, alkyl, alkenyl, cycloalkyl, cycloalkenyl, aryl, heteroaryl or heterocyclyl; and
a=1.

Suitably R$_1$ represents H or alkyl, such as H or methyl, especially H.

Suitably R$_3$ represents H or alkyl, such as H or methyl, especially H.

Suitably Z represents O.

R$_2$ may, for example, represent C$_{3-4}$alkenyl e.g., CH$_2$CH=CH$_2$ or C$_{1-4}$alkyl e.g., n-propyl or t-butyl.

Exemplary compounds of Formula VIII are as follows:
(2S)-2-amino-3-(4-azido-2-{[(prop-2-en-1-yloxy)carbonyl]amino}butanamido)propanoic acid Formula VIII.1

(2S)-2-amino-3-{4-azido-2-[(propoxycarbonyl)amino]butanamido}propanoic acid

Formula VIII.2 and
(2S)-2-amino-3-{4-azido-2-[(t-butoxycarbonyl)amino]butanamido}propanoic acid Formula VIII.3

In structures of Formulae I to VI and X, when FG represents alkene, it suitably represents —CH=CH$_2$ or —CH=CH—CH$_3$, preferably —CH=CH$_2$. Examples of —(CH$_2$)$_b$-FG and —(CH$_2$)$_d$-FG are —CH$_2$—CH=CH$_2$ and —CH$_2$—CH$_2$—CH=CH$_2$.

In structures of Formulae I to VI and X, when FG represents alkyne, it suitably represents —C≡CH or —C≡C—CH$_3$, preferably —C≡CH. An example of —(CH$_2$)$_b$-FG and —(CH$_2$)$_d$-FG is —CH$_2$—C≡CH.

In structures of Formulae I to VI and X, when FG represents ketone, it suitably represents —C(=O)—CH$_3$ or —C(=O)—CH$_2$—CH$_3$, preferably —C(=O)—CH$_3$.

In structures of Formulae I to VI and X, when FG represents ester, it suitably represents —C(=O)—Oalkyl e.g., —C(=O)—Omethyl.

In structures of Formulae I to VI and X, when FG represents aryl, it suitably represents phenyl substituted by halogen, especially iodine (e.g., 4-iodo-phenyl).

In structures of Formulae I to VI and X, when FG represents cycloalkyne, it suitably represents cyclooctyne, e.g., cyclooct-4,5-yne.

In structures of Formulae I to VI and X, when FG represents azide, an example of —(CH$_2$)$_b$-FG or —(CH$_2$)$_d$-FG is —(CH$_2$)$_2$—N$_3$.

In structures of Formulae VII and VIII when R, R$^1$, R$^2$ and R$^3$ represent aryl, it suitably represents phenyl.

The pyrrolysine analogs disclosed herein can be made using various methods. The reaction conditions can generally be determined by one of the ordinary skill in the art.

Formula I analogs are readily prepared by the addition of an activated carbonyl group, such as a chloroformate, activated carboxylic acid ester, isocyanate, activated carbonate or sulfonyl halide to a mono-protected diamino substrate of type 1, in which the α-amino group is protected by a protecting group ("PG") such as a Boc, Cbz, TFA, Acetyl or Fmoc group (see Scheme 1). The coupled product 3 can undergo further modifications, such as the displacement of halides with an azido nucleophile to install the desired functionality. Otherwise, the intermediate 3 is deprotected to remove the α-amino acid masking group to afford the desired Formula 1 analog.

Scheme 1:

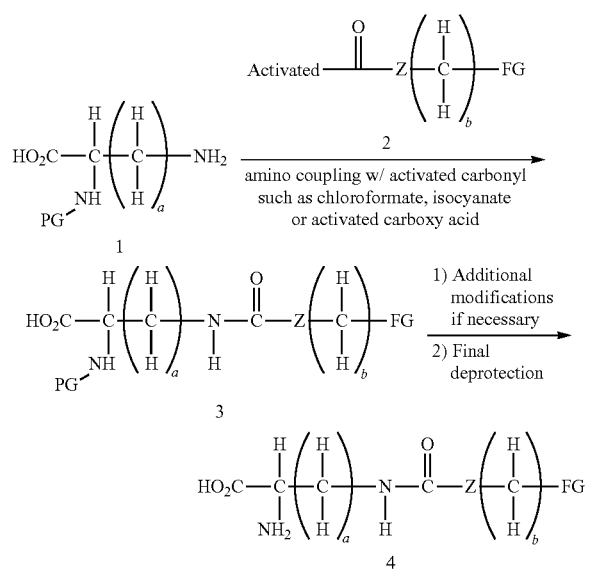

Formula VII analogs are readily prepared by first preparing the desired α-azido precursor. One strategy for accomplishing this is to displace a leaving group (LG) such as a halide (Cl, Br, or I) or alkyl sulfonate (tosylate, mesylate, triflate) with sodium azide to afford the α-azido acid 6. This can then be coupled to a mono-protected diamino substrate of type 7 by activating the carboxylic acid with a group such as HBTU, DCC and NHS or CDI. The product 8 is obtained by removing the protecting group masking the α-amino group. Protecting groups may be used as per Scheme 1. See Scheme 2:

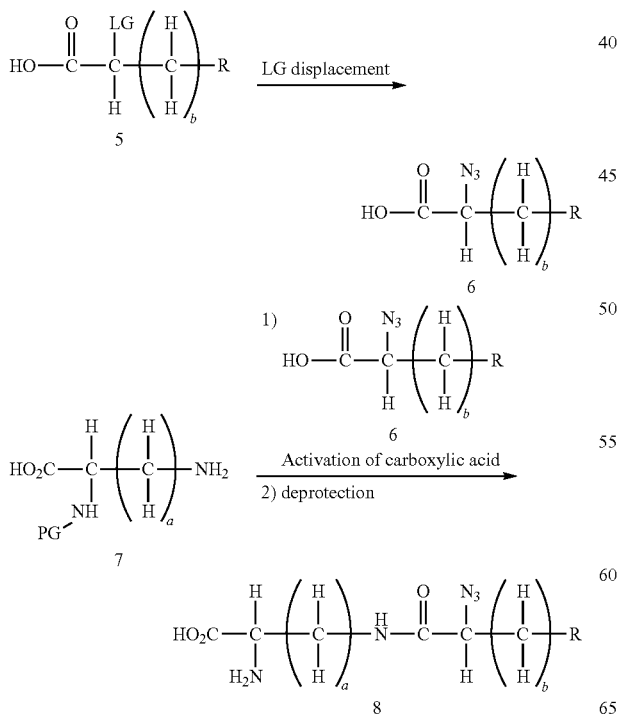

Formula II analogs were prepared by conjugation of hydroxyl amino acids 9 to substrates with activated carbonyls such as carboxylic acid ester, isocyanate, acid chlorides, activated carbonates or sulfonyl halides 10. The coupled product 11 can undergo further modifications, such as the installation of the azide functional group by displacement of leaving groups such as halides or activated alcohols. The desired amino acid analog 12 is obtained by final deprotection to remove the α-amino acid masking group. Protecting groups may be used as per Scheme 1. See Scheme 3:

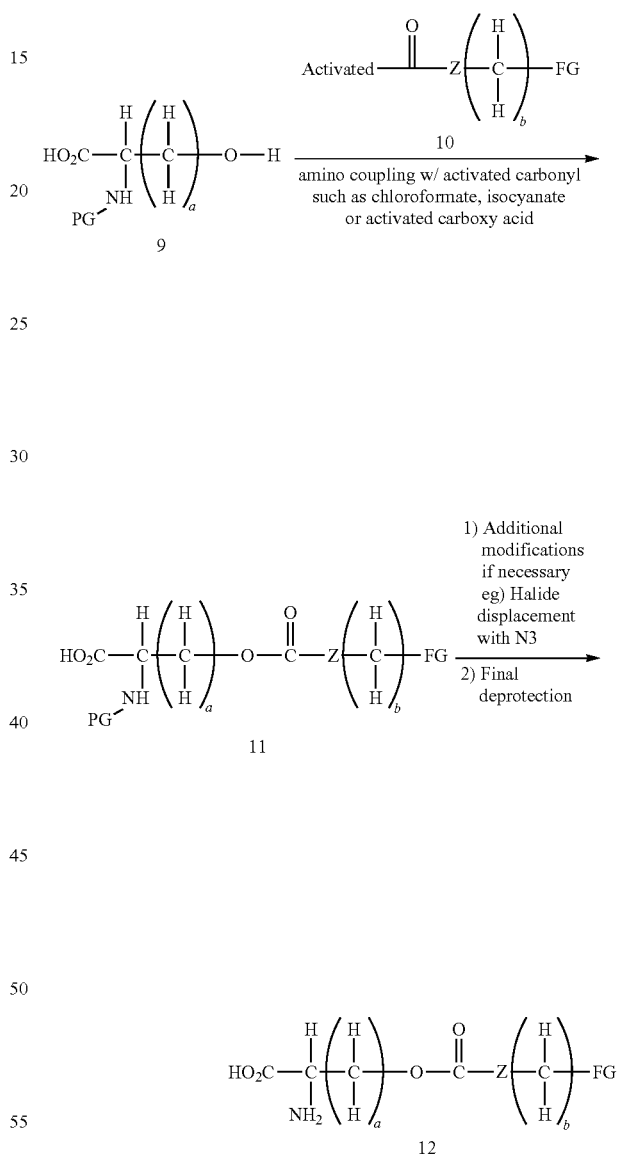

Formula III analogs which contain a thioether linkage are readily prepared by a key S-alkylation step. A thioamino acid such as cysteine 13 is treated with the desired functionalized alkylating agent 14 to affect the S-alkylation. Additional functionalization is then done to fix the amino acid in its final form (e.g., installation of azide group). Final deprotection as necessary reveals the desired amino acid 16. Protecting groups may be used as per Scheme 1.

See Scheme 4:

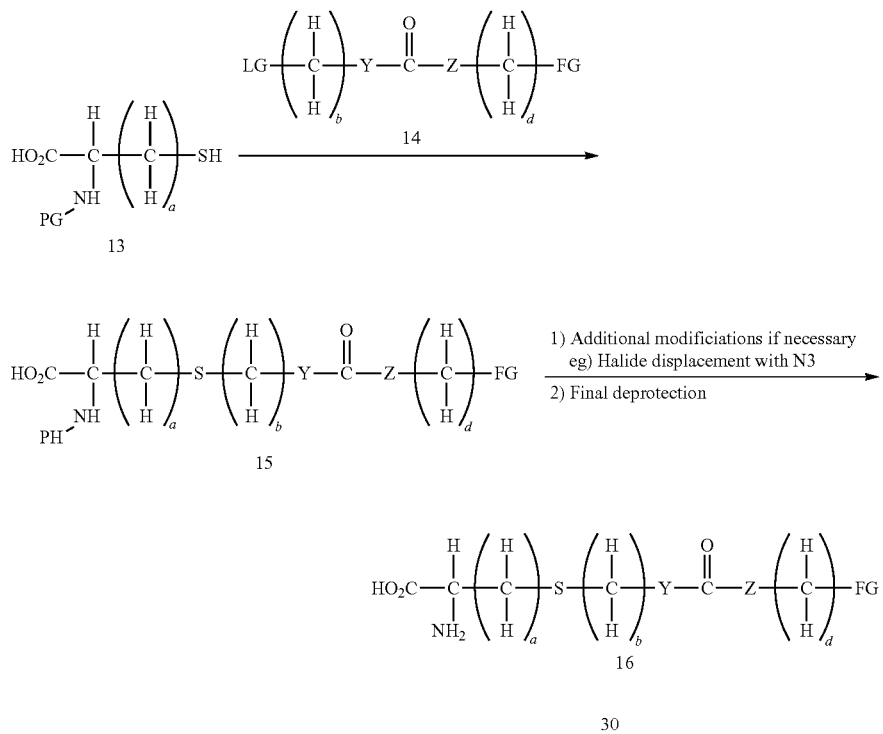

Formula IV analogs can be prepared in an analogous fashion to cysteine analogs in which the ether linkage is prepared by hydroxyl alkylation. A protected hydroxyl amino acid such as serine 17 is treated with alkylating agent 18 to affect the O-alkylation. Additional functionalization is then done to fix the amino acid in its final form (e.g., installation of azide group). Final deprotection as necessary reveals the desired amino acid 20. Protecting groups may be used as per Scheme 1. See Scheme 5:

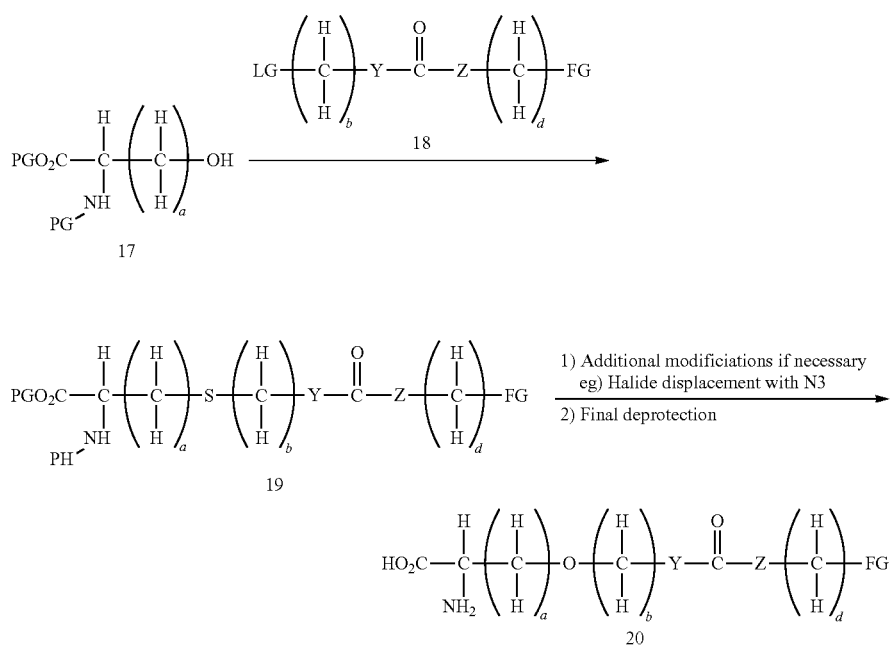

Formula V analogs were prepared in a straightforward manner by a key peptide coupling with a monoprotected diamino derivative 24. The process begins with the coupling of bifunctional amine such as an α or β amino acid 21 to a activated carbonyl such as carboxylic acid ester, isocyanate, acid chlorides, activated carbonate or sulfonyl halides to afford intermediate 23. The carboxylic acid of 23 is then activated with a reagent or combination of reagents such as HBTU, DCC and NHS or CDI and used to acylate the monoprotected diamine such as diaminopropionic acid 24 to afford the peptide 25. The intermediate 25 is either deprotected or further functionalized (e.g., azidonation) just prior to deprotection to the desired amino acid 26. Protecting groups may be used as per Scheme 1. See Scheme 6:

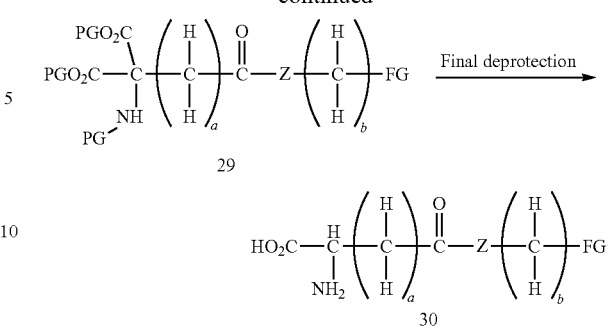

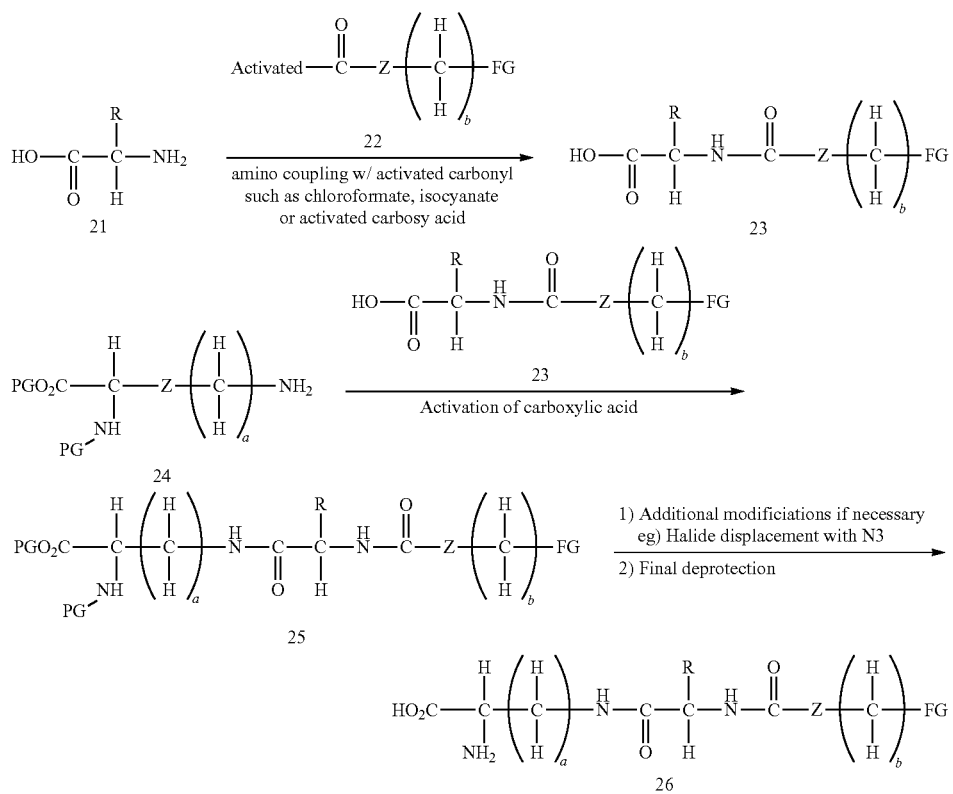

Formula VI analogs can be prepared by alkylation of the α-center of a glycine equivalent. In this sequence a protected glycine equivalent such as diethylacetamidomalonate 27 is treated with an alkylating agent such as 28 under basic conditions to effect alkylation at the α-position of the glycine derivative. Subsequent deprotection under acidic or basic conditions affords the desired amino acid 30.

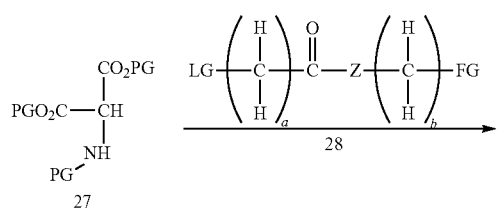

Formula VIII analogs were prepared by coupling an azidohomoalanine derivatives to the sidechain amine of a bifunctional amine such as 24. The process begins with the coupling of azidohomoalanine 31 with an activated carbonyl such as a carboxylic acid ester, isocyanate, acid chlorides, activated carbonate or sulfonyl halides to afford intermediate 33. The carboxylic acid of 33 is then activated with a reagent or combination of reagents such as HBTU, DCC and NHS or CDI and used to acylate the monoprotected diamine such as diaminopropionic acid 24 to afford the peptide 34. The intermediate 34 is deprotected to afford 35. Protecting groups may be used as per Scheme 1.

See Scheme 8:

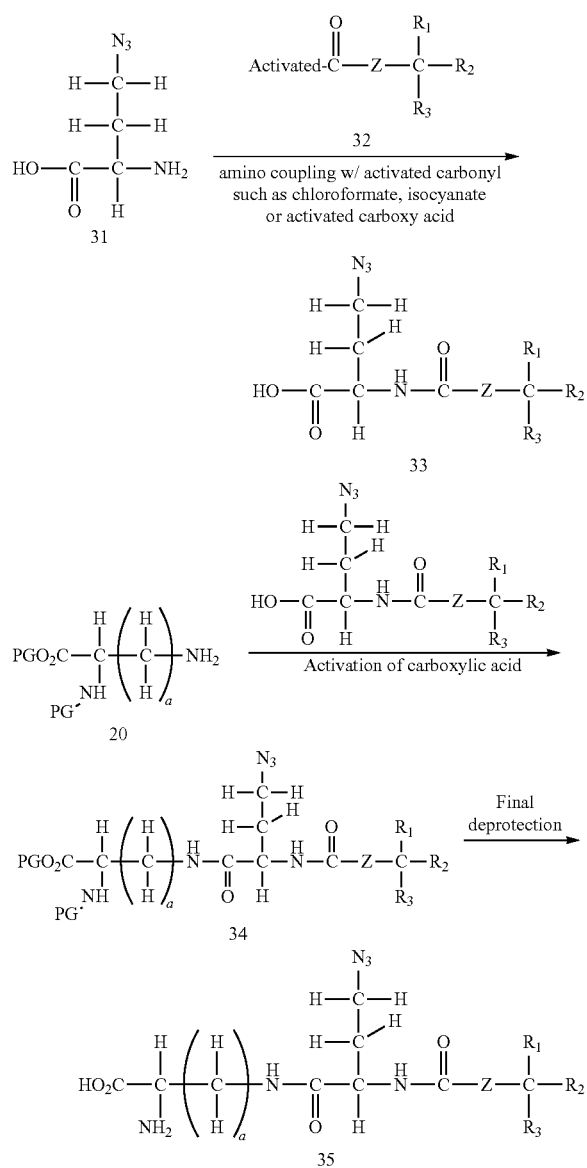

Incorporation of Non-Natural Amino Acid into Proteins

The pyrrolysine analogs disclosed herein can be incorporated into recombinant proteins. In particular, site specific incorporation of the analog into a recombinant protein can be achieved through amber suppression, wherein a nonsense (amber) codon is inserted within the nucleotide sequence encoding the recombinant protein, at a site where the pyrrolysine analog is to be inserted. The mutated nucleotide sequence, along with one or more plasmids encoding the PylRS and tRNApyl are inserted into a cell of a cell free expression system.

The host cell may be a eukaryotic cell line which is transformed with a vector comprising a DNA construct as aforesaid.

Alternatively, a cell-free expression system is provided, wherein a synthesis reaction lysate obtained from a host cell comprises at least one component required for the synthesis of polypeptides. The synthesis reaction lysate is obtained from bacterial or eukaryotic cells.

Preferably, the synthesis reaction lysate is obtained from eukaryotic cells, more preferably, from rabbit reticulocytes or wheat germ.

Preferably, the cell-free expression system is capable of expressing WT PylRS and tRNApyl of the present invention, wherein tRNApyl is introduced into the cells used to obtain the synthesis reaction lysate with DNA constructs of the invention.

Cell-free expression systems suitable for use in the present invention are described for instance in WO201008110, WO2010081111, WO2010083148, incorporated in their entirety herein by reference.

When the pyrrolysine analog is added to the cell or expression system, said analog is incorporated in the recombinant protein at the specified position. The nnAA and the tRNApyl are bound by the pylRS and the tRNApyl is subsequently aminoacylated with the nnAA. This tRNApyl containing an amber anticodon is released into the cytosol where in response to an amber stop codon can interact with the ribosome and the nnAA released to form a peptide bond with the growing polypeptide chain.

Recombinant proteins modified to incorporate a pyrrolysine analog of the invention include all recombinant proteins amenable to site specific post translational modifications, e.g., therapeutic proteins, for instance cytokines, antibodies and antibody derivatives (such as Fab fragments, or single chain antibodies, e.g., single chain variable fragments (scfvs)), peptides, enzymes, fusion proteins, decoy receptors, protein vaccines, protein hormones, e.g., insulin, growth factors, (e.g., human growth hormone, hGH, hGCSF, hFSH, hHCG). Further proteins modifiable with pyrrolysine analogs of the invention include diagnostic labels, imaging reagents.

Suitably, proteins may be modified site specifically to incorporate one or more than one nnAA (pyrrolysine analog) of the invention. For instance, an antibody may incorporate a nnAA of the invention at the heavy chain, or at the light chain, or at both light and heavy chain.

Site Specific Conjugation of Proteins with Incorporated Non-Natural Amino Adds

Proteins having incorporated pyrrolysine analogs of the present invention may be used for the preparation of functionalized protein conjugates. Molecules that may be conjugated to proteins having incorporated non-natural amino adds include (i) other proteins, e.g., antibodies especially monoclonal antibodies; (ii) polymers e.g., PEG groups or other groups that may cause half life extension in the system; (iv) cytotoxic agents e.g., Auristatin F; and (v) drug moieties e.g., doxorubicin and moieties containing radioactive isotopes. Moreover these modified proteins can be conjugated to drugs or nucleotides for targeted delivery of these potent compounds.

More details of certain embodiments are given below in the discussion of antibody drug conjugates.

Pyrrolysine analogs may conveniently contain a unique chemical group permitting conjugation in a targeted fashion without risk of side reaction with other amino acids. For example non-natural amino acids may contain azide or alkyne groups permitting reaction with a molecule to be conjugated which contains a corresponding alkyne or azide group using the Huisgen 1,3-dipolar cycloaddition reaction.

Preferred conjugation chemistries of the invention include reactions which are orthogonal to the natural twenty amino acids. Such reactions do not interact or cause side reactions with the native 20 amino acids, they are specific to the functional groups associated with the reaction. Suitably the necessary functional groups are incorporated into the target protein via the pyrrolysine analogs of the present invention.

Further, said reactions proceed under conditions which are not destructive to the protein, for instance aqueous solvents, with a pH range which is acceptable to the protein and maintains its solubility, at a temperature which does not lead to deleterious effects upon the protein.

Increasing the stability of the attachment moiety between the protein and the linker can be advantageous. Conventional methods conjugate to the thiol groups of cysteine by reaction with a maleimide forming a thiol ether. The thiol ether can undergo the reverse reaction releasing the linker drug derivative from the antibody. In an embodiment of the invention, the conjugation chemistry employed between an azide and an alkyne results in an aromatic triazole which is significantly more stable, and not as prone to reversibility.

In addition, the product of the reaction, the linkage between protein and payload, ought to be stable, equal to or greater than the stability associated with conventional linkages (amide, thiol ether). Though not an impediment to conjugation, it is often advantageous if the conjugation reactions can be done under native conditions, as this will eliminate an extra refolding processing step.

Preferred chemical conjugations for production of conjugates of the invention include: a 3+2 alkyne-azide cycloaddition; 3+2 dipolar cycloaddition; Husigen 3+2 cycloaddition; Copper promoted azide-alkyne cycloaddition (CuAAC); Ruthenium promoted azide alkyne cycloaddition (RAAC); metal promoted azide alkyne cycloaddition (MAAC); strain promoted azide alkyne cycloaddition (SPAAC); palladium based couplings including the Heck reaction, Sonogashira reaction, Suzuki reaction, Stille coupling, Hiyama/Denmark reaction olefin metathesis, Dielsalder reaction carbonyl condensation with hydrazine, hydrazide, alkoxy amine or hydroxyl amine; strain promoted cycloadditions with nitriles and nitrile oxides; electron promoted cycloaddition; fragment extrusion cycloaddition; alkene cycloaddition followed by a β-elimination reaction.

According to one preferred embodiment, the incorporated amino acid contains an azide or an alkyne group and the process of chemical modification comprises reacting said azide or alkyne group with a reagent comprising an alkyne or azide group. The envisaged reaction is a Huisgen 1,3-dipolar cycloaddition reaction which leads to production of a triazole linkage. The reagent comprising an alkyne or azide group may be a protein (e.g., an antibody) or a cytotoxic agent or a drug or a substance suitable for half life extension (e.g., a PEG group) which carries an alkyne or azide group optionally via a linker.

The site specific conjugations between the incorporated nnAA and the target payload can be done with fully folded proteins such as antibodies, antibody fragments, and cytokines. Alternatively, the conjugation can be done on denatured proteins in the presence of denaturants such as sodium dodecylsulfate and urea. The copper catalyzed azide alkyne addition can be done in the presence of denaturants and reducing agents such as dithiothreitol and 2-mercaptoethanol.

When more than one nnAA is incorporated into a target protein (e.g., an antibody), the chemical modification may be the same or different. For example if two nnAAs are incorporated, one may be modified to be conjugated to a drug moiety and one may be modified to be conjugated to a PEG moiety.

Conveniently, upon incorporation of more than one nnAA of the invention bearing different but complementary reactive groups, said nnAAs can react with each other to generate an intramolecular link.

In an embodiment, conjugation chemistry of the invention is used for preparing an antibody drug conjugate. The conjugation chemistry may also be used to assemble antibody-protein conjugates, protein protein conjugates such as bispecifics composed of antibody fragments. The conjugation chemistry may also be used to conjugate polymer bond drug conjugates to targeting agents such antibodies and antibody fragments. The conjugation chemistry can also be used to attach polymers such as PEG to proteins to manipulate pharmacokinetic properties.

PEG Moieties

Target proteins may be conjugated to PEG moieties. PEG moieties may be incorporated into antibody drug conjugates. The PEG moiety may typically have a molecular weight ranging between 5 kDa and 40 kDa, More preferably, the PEG moiety may have a molecular weight of around 20 kDa. PEG moieties may be straight chain or branched.

Antibody Drug Conjugates (ADCs)

Pyrrolysine analogs according to the invention are particularly useful for production of Antibody Drug Conjugates (recombinant antibody covalently bound by a synthetic linker to a given drug, typically a cytotoxic drug, or else a protein or a PEG group) which are homogeneous nature, in which the number of drugs (or other conjugated molecule) per antibody and position of those drugs upon the antibody are explicitly controlled, whereby monoclonal antibodies containing incorporated non-natural amino acids are obtained and site specifically conjugated to a linker carrying a drug moiety (or other conjugated molecule) through orthogonal chemistry.

ADCs obtained with pyrrolysine analogs of the present invention may be manufactured following methods including the following steps:

1. Introducing into a stable cell line of the invention one or more plasmids carrying the DNA sequence coding for a full length antibody, whereby a stop codon is introduced at specific positions within the sequence
2. Purify the modified antibody with the pyrrolysine analog (nnAA) installed at desired position(s).
3. React a cytotoxin-linker derivative modified to include a functional group complimentary to the nnAA installed in the antibody with the modified antibody containing a complementary reactive group through an orthogonal chemistry
4. Purify the resulting ADC Thus, the present invention also provides ADCs whereby the antibody component has been modified to incorporate non natural amino acids bearing a unique reactive functional group at desired positions, whereby such functional group allows conjugation to a drug moiety (or protein or PEG group).

In an embodiment the present invention provides an antibody conjugate comprising an anti-Her-2 antibody which is conjugated to one or more moieties (e.g., one, two, three or four, preferably one or two, especially one) selected from protein, drug and PEG moieties via linkers comprising a triazole moiety.

In particular, the triazole moiety may be formed by reaction of an azide or alkyne moiety in the side chain of a non-natural amino acid incorporated into the sequence of the anti-Her-2 antibody and an alkyne or azide moiety attached to the protein, drug or PEG moiety.

In one embodiment, the triazole moiety is formed by reaction of an azide or alkyne moiety in the side chain of a non-natural amino acid incorporated into the sequence of the anti-Her-2 antibody and an alkyne or azide moiety attached to the protein, drug or PEG moiety under conditions of Cu(I) catalysis.

In one embodiment a copper azide alkyne cycloaddition is used for the conjugation. Suitably, the reaction utilizes a cytotoxic agent such as auristatin, amanitin, taxol or doxorubicin bearing a terminal alkyne. Further, the reaction employs a copper source such as copper sulfate, copper acetate, copper iodide or copper bromide; a reducing agents such as sodium ascorbate, hydrazine, hydroxylamine, sodium bisulfite, dithiothreitol, cysteine, b-mercaptoethanol; a copper chelating ligand such as Tris[(1-benzyl-1H-1,2,3-triazol-4-yl)methyl]amine (TBTA) or Tris(3-hydroxypropyltriazolylmethyl)amine (THPTA). Suitably, the reaction may be performed at 4-50° C. Suitably, the reaction time ranges from 0.5 to 48 hrs. In an alternative embodiment, a strain promoted azide alkyne cycloaddition is used for conjugation. Suitably, the reaction utilizes a dye, a PEG polymer, or cytotoxic agent such as auristatin bearing a cyclooctyne group. Suitably, the reaction is allowed to incubate at room temperature for 0.5-48 hrs.

Salts

Pyrrolysine analogues described herein may optionally be employed in the form of a salt. Any such salts form an aspect of the invention. Salts of carboxylic acids may include salts formed with Group 1 and Group 2 metals, especially soluble salts such as sodium and potassium salts. Salts of amines may include salts formed with weak and strong acids, such as HCl, HBr or acetic acid.

Embodiments of the Invention

Embodiments of the invention are represented as follows:
1. A pyrrolysine analogue of formula I:

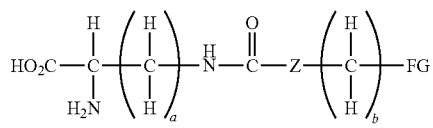

wherein
Z=bond, $CH_2$, $CH-NH_2$, $CH-OH$, NH, O, S or $CH-NH_2$;
a is an integer 3-7;
b is 0 or an integer 1-7; and
FG=azide, alkene, alkyne, ketone, ester, aryl or cycloalkyne.
2. A pyrrolysine analogue according to embodiment 1 wherein a is 3.
3. A pyrrolysine analogue according to embodiment 1 wherein a is 4.
4. A pyrrolysine analogue according to embodiment 3 selected from Formula IA.4

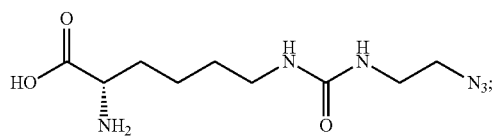

Formula IA.5

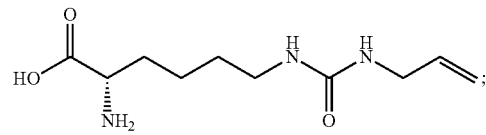

Formula IA.6

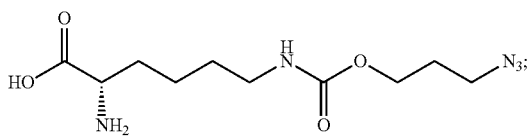

Formula IA.7

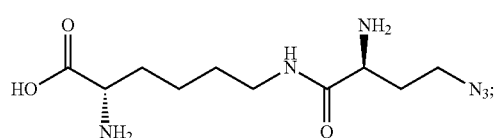

Formula IA.8

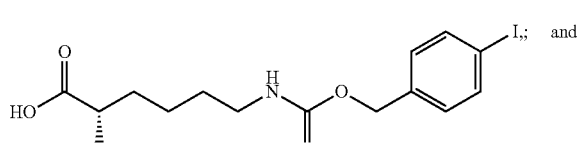

Formula IA.9

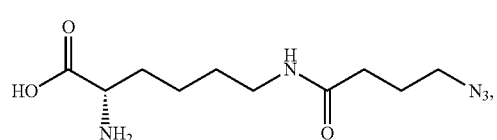

5. A pyrrolysine analogue according to embodiment 2 selected from

Formula IB.1

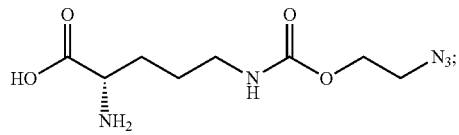

Formula IB.2

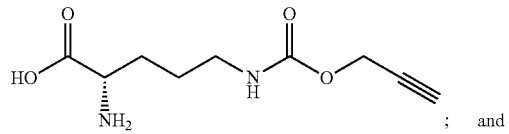

Formula IB.3

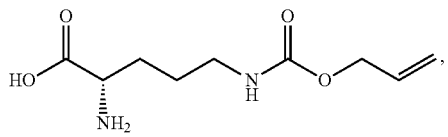

6. A pyrrolysine analogue of formula II:

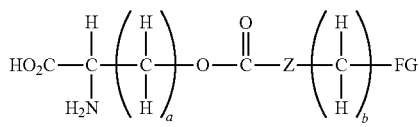

wherein
Z=$CH_2$, CH—$NH_2$, CH—OH, NH, O or S;
FG=azide, alkene, alkyne, ketone, ester, aryl or cycloalkyne;
a=an integer 3 or 5-7; and
b=an integer 1-4.

7. A pyrrolysine analogue of formula III:

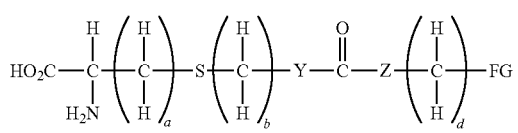

wherein
Y=$CH_2$, NH, O or S;
Z=$CH_2$, CH—$NH_2$, CH—OH, NH, O or S;
FG=azide, alkene, alkyne, ketone, ester, aryl or cycloalkyne;
a=an integer 1-7;
b=an integer 1-7 save that when Z is NH, O or S then b is an integer 2-7;
provided that a+b is in the range 2-8;
and d=an integer 1-4.

8. A pyrrolysine analogue according to embodiment 7 selected from

Formula III.1
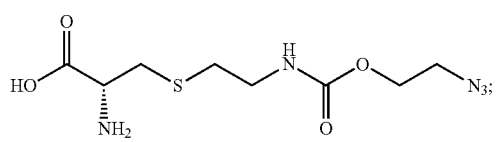

Formula III.2
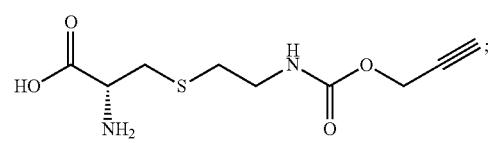

Formula III.3
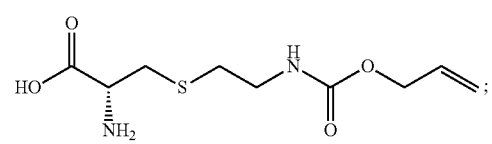

Formula III.4
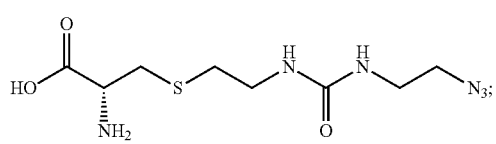

Formula III.5
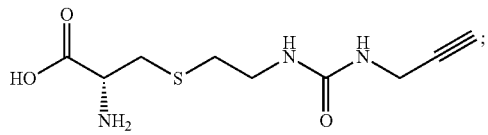

Formula III.6
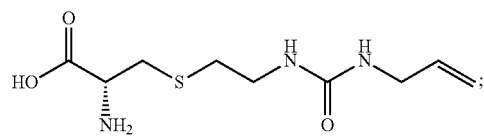

Formula III.7
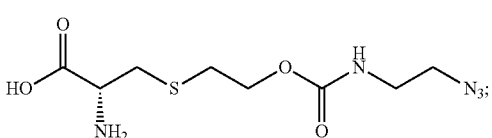

Formula III.8
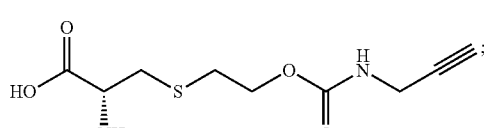

Formula III.9
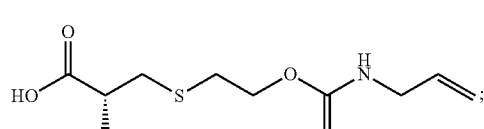

Formula III.10
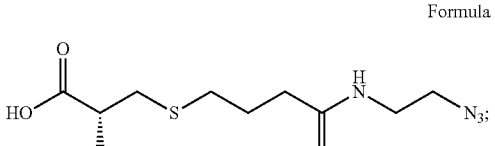

Formula III.11
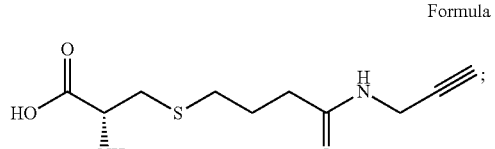

Formula III.12
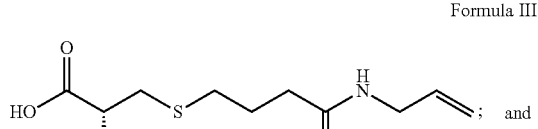
; and

Formula III.13
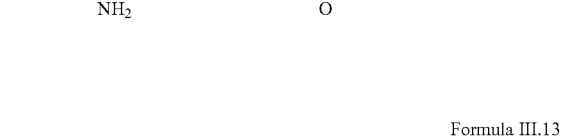

9. A pyrrolysine analogue of formula IV:

$$HO_2C-\underset{H_2N}{\underset{|}{C}}H-\left(\underset{H}{\underset{|}{C}}H\right)_a-S-\left(\underset{H}{\underset{|}{C}}H\right)_b-Y-\underset{}{\overset{O}{\underset{|}{C}}}-Z-\left(\underset{H}{\underset{|}{C}}H\right)_d-FG$$

wherein
Y=$CH_2$, NH, O or S;
Z=$CH_2$, CH—$NH_2$, CH—OH, NH, O or S;
FG=azide, alkene, alkyne, ketone, ester, aryl or cycloalkyne;
a=an integer 1-7;
b=an integer 1-7 save that when Z is NH, O or S then b is an integer 2-7;
provided that a+b is in the range 2-8;
and
d=an integer 1-4.

10. A pyrrolysine analogue according to embodiment 9 selected from

Formula IV.1

Formula IV.2

Formula IV.3

Formula IV.4

Formula IV.5

Formula IV.6

Formula IV.7

Formula IV.8

Formula IV.9

Formula IV.10

Formula IV.11

Formula IV.12

11. A pyrrolysine analogue of formula V:

$$HO_2C-\underset{H_2N}{\underset{|}{C}}H-\left(\underset{H}{\underset{|}{C}}H\right)_a-N\underset{H}{\overset{}{-}}\underset{}{\overset{R}{\underset{|}{C}}}H-\underset{}{\overset{O}{\underset{|}{C}}}-N\underset{H}{\overset{}{-}}\underset{}{\overset{O}{\underset{|}{C}}}-Z-\left(\underset{H}{\underset{|}{C}}H\right)_b-FG$$

wherein
R=the side chain of one of the 20 natural amino acids;
Z=$CH_2$, CH—$NH_2$, CH—OH, NH, O or S;
FG=azide, alkene, alkyne, ketone, ester, aryl or cycloalkyne;
a=1; and
b=an integer 1 to 4.

12. A pyrrolysine analogue according to embodiment 11 selected from

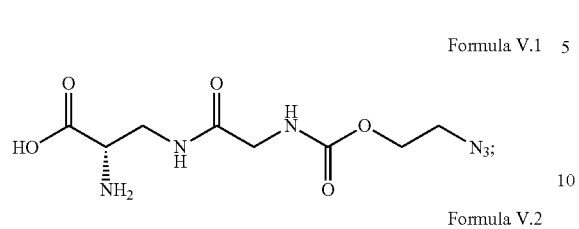
Formula V.1

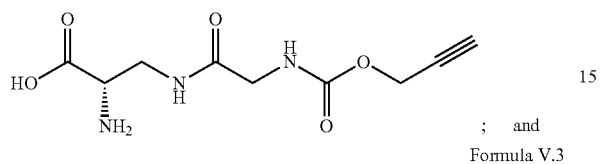
Formula V.2

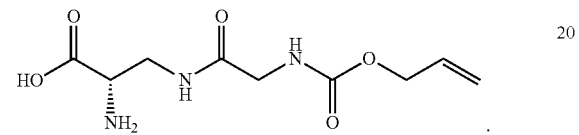
Formula V.3

13. A pyrrolysine analogue of formula VI:

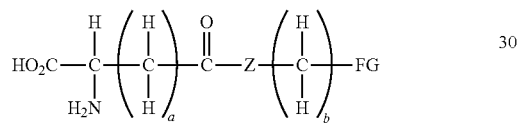

wherein
Z=CH$_2$, CH—NH$_2$, CH—OH, NH, O or S;
FG=azide, alkene, alkyne, ketone, ester, aryl or cycloalkyne;
a=4 or 5; and
b=an integer 1 to 4;

14. A pyrrolysine analogue according to embodiment 13 selected from

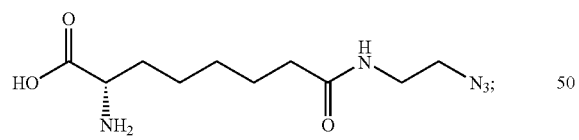
Formula VI.1

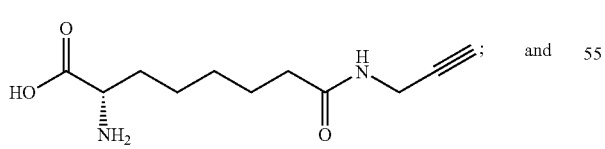
Formula VI.2

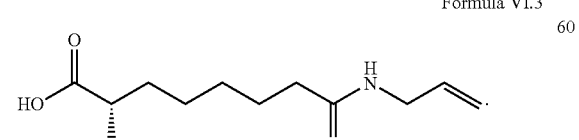
Formula VI.3

15. A pyrrolysine analogue of formula VII:

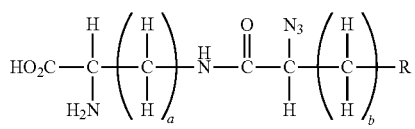

wherein
R=alkyl, alkenyl, cycloalkyl, aryl, heteroaryl or heterocyclyl;
a=an integer 1 to 7; and
b=an integer 1 to 3.

16. A pyrrolysine analogue according to embodiment 15 which is:

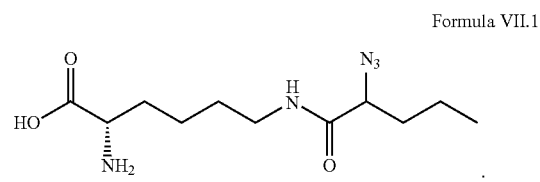 [SMILES: CCCC(N=[N+]=[N-])C(=O)NCCCC[C@H](N)C(=O)O]
Formula VII.1

17. A pyrrolysine analogue of formula VIII:

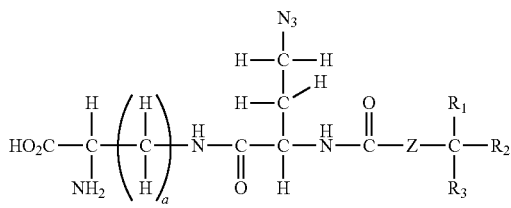

wherein
Z=CH$_2$, CH—NH$_2$, CH—OH, NH, O or S;
R$_1$=H, alkyl, alkenyl, cycloalkyl, cycloalkenyl, aryl, heteroaryl or heterocyclyl;
R$_2$=alkyl, alkenyl, cycloalkyl, cycloalkenyl, aryl, heteroaryl or heterocyclyl;
R$_3$=H, alkyl, alkenyl, cycloalkyl, cycloalkenyl, aryl, heteroaryl or heterocyclyl; and
a=1.

18. A pyrrolysine analogue according to embodiment 17 selected from

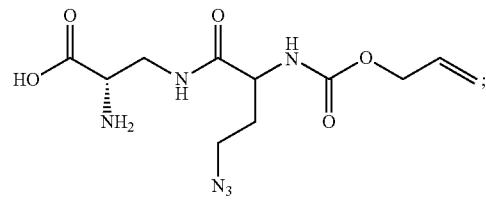
Formula VIII.1

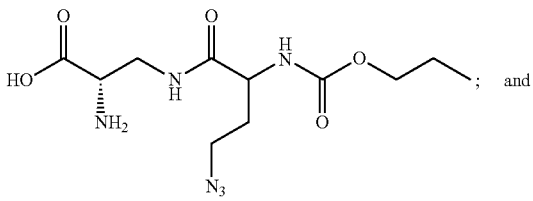
Formula VIII.2

Formula VIII.3

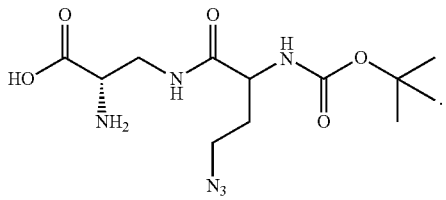

19. A mutant protein containing as non-natural amino acid one or more pyrrolysine analogues according to any one of embodiments 1 to 18.
20. A mutant protein according to claim 19 containing as non-natural amino acid one pyrrolysine analogue according to any one of embodiments 1 to 18.
21. A mutant protein according to embodiment 19 or embodiment 20 which is conjugated via the one or more non-natural amino acids to one or more moieties selected from proteins, cytotoxic agents, drugs and polymers.
22. A mutant protein according to embodiment 21 which is conjugated to a PEG moiety.
23. A mutant protein according to embodiment 21 which is conjugated to an antibody moiety.
24. A mutant protein according to embodiment 21 which is conjugated to a cytotoxic agent moiety.
25. A mutant protein according to embodiment 21 which is conjugated to a drug moiety.
26. Use of a pyrrolysine analogue according to any one of embodiments 1 to 18 in the manufacture of a mutant protein containing one or more non-natural amino acids.

EXAMPLES

Example 1. Preparation of Formula I and IB Analogs

Preparation of (2S)-2-amino-6-[(2S)-2-amino-4-azidobutanamido]hexanoic Acid (Formula IA.7)

In a 20 mL vial with magnetic stirrer was placed N-Boc-azidohomoalanine (200 mg, 1 eq) and HBTU (311 mg, 1 eq) in 4 mL of DMF. The mixture was stirred for 15 min and then a solution N-Boc-Lysine (235 mg, 1 eq) in DMF (3 mL) was added, followed by triethylamine (228 uL). The vial was capped and stirred for 4 h. The mixture was partitioned between 250 mM citric acid and ethyl acetate. The organic layer was retained and the aqueous layer was extracted two additional times with ethyl acetate. The organic layers were combined, dried with sodium sulfate, filtered and concentrated. Mass spectrometry indicated the formation of the desired intermediate. Additional purification was conducted via silica gel chromatography.

The Boc protected intermediate was placed in a 20 mL vial and suspended in acetonitrile (4 mL). To this was added a solution of hydrochloric acid in dioxane (4N, 4 mL). The solution was stirred for 2 h and then concentrated under reduced pressure. The mixture was lyophilized. Additional purification by ion exchange resin (Dowex-50) afforded the desired amino acid. The product was confirmed by mass spectrometry.

Preparation of ((2S)-2-amino-6-{[(2-azidoethyl)carbamoyl]amino}hexanoic Acid (Formula IA.4)

In a 4 mL vial with magnetic stirrer was placed Boc-N-6-Lysine (50 mg, 1 eq) and DMF (1 mL). To this was added 2-chloroethyl isocyanate (17.3 mg, 1.0 eq) and pyridine (32.3 uL, 2 eq). The vial was capped and allowed to stir for 4 h. The solution was transferred to an extraction funnel, diluted with ethylacetate and 100 mM citric acid. The mixture shaken and the layers separated. The aqueous layer was extracted with ethyl acetate two additional times. The organic layers combined, washed with 5% lithium chloride, dried with sodium sulfate, filtered and concentrated. The product was identified by mass spectrometry and taken forward into the next step directly.

In a 4 mL vial with magnetic stirrer was placed the crude chloro derivative and DMSO (1 mL). Sodium azide (130 mg, 5 eq) and pyridine (32.3 uL, 2 eq) were added to the mixture and the vial was capped. The mixture was stirred overnight at 60° C. The mixture was transferred to an extraction funnel and diluted with 100 mM citric acid and ethyl acetate. The mixture was shaken and the layers separated. The aqueous layer was extracted with ethyl acetate two additional times. The organic layers combined, washed with 5% lithium chloride, dried with sodium sulfate, filtered and concentrated. The intermediate was identified by mass spectrometry and carried on to the next step.

In a 20 mL vial was placed the crude and acetonitrile (2 mL). To this was added a solution of hydrochloric acid in dioxane (4N, 2 mL). The solution was stirred for 2 h and then concentrated under reduced pressure. The mixture was lyophilized to a semi solid and used in translational testing. The product was confirmed by mass spectrometry.

Preparation of (2S)-2-amino-6-{[(prop-2-en-1-yl)carbamoyl]amino}hexanoic Acid (Formula IA.5)

In a 4 mL vial with magnetic stirrer was placed Boc-N-6-hydroxynorleucine (50 mg, 1 eq) and DMF (1.5 mL). To this was added allyl isocyanate (18.0 uL, 1.0 eq) and pyridine (32.3 uL, 2 eq). The vial was capped and allowed to stir for 4 h. The solution was transferred to an extraction funnel, diluted with ethylacetate and 100 mM citric acid. The mixture shaken and the layers separated. The aqueous layer was extracted with ethyl acetate two additional times. The organic layers combined, washed with 5% lithium chloride, dried with sodium sulfate, filtered and concentrated. The product was identified by mass spectrometry and taken forward into the next step directly.

In a 20 mL vial was placed the crude hydroxyl leucine-allyl carbamate derivative in acetonitrile (2 mL). To this was added a solution of hydrochloric acid in dioxane (4N, 2.5 mL). The solution was stirred for 2 h and then concentrated under reduced pressure. The mixture was lyophilized to a semi solid and used in translational testing. The product was confirmed by mass spectrometry. Additional purification could be done with ion exchange chromatography (DOWEX-50).

Preparation of (2S)-2-amino-5-{[(2-azidoethoxy)carbonyl]amino}pentanoic Acid (Formula IB.1)

In a 20 mL vial with magnetic stirrer was placed N-Boc-Ornithine (500 mg, 1 eq) in a solution of potassium carbonate (1M, 2.5 mL) and dioxane (2.5 mL). 2-chloroethyl chloroformate (223 uL, 1 eq) was added and the vial was capped and stirred for 4 h. The mixture was acidified to near pH 2 with 1M Citric acid. The solution was transferred to an extraction funnel and the aqueous layer extracted with ethyl acetate (3×). The organic layers combined, dried with sodium sulfate and concentrated. LC/MS confirmed the major product was the desired mass. The crude intermediate was carried forward to the next step without additional purification.

The crude chloride intermediate was placed in a 20 mL vial and dissolved in DMSO (15 mL). Sodium azide (625 mg, 4 eq) and pyridine (155 uL) were added and the vial was capped and stirred overnight at 60° C. The mixture was poured into an extraction funnel with 250 mM citric acid and extracted with ethyl acetate (3×). The organic layers were combined, dried with sodium sulfate and concentrated. LC/MS confirmed the formation of the product. Additional purification was conducted via silica gel chromatography.

The Boc Intermediate was placed in a 20 mL vial and suspended in acetonitrile (4 mL). To this was added a solution of hydrochloric acid in dioxane (4N, 4 mL). The solution was stirred for 2 h and then concentrated under reduced pressure. The concentrate was taken up in water and applied to an ion exchange resin (Dowex-50). The capture material was washed with water and eluted with ammonium bicarbomnate. The enriched fractions with the amino acid were identified by TLC, pooled and lyophilized to afford the desired product. The product was confirmed by mass spectrometry.

Preparation of (2S)-2-amino-5-{[(prop-2-ent-yloxy)carbonyl]amino}pentanoic Acid (Formula IB.3)

In a 20 mL vial with magnetic stirrer was placed N-Boc-Ornithine (300 mg, 1 eq) in a solution of potassium carbonate (1M, 2 mL) and dioxane (2 mL). Allyl chloroformate (137 uL, 1 eq) was added and the vial was capped and stirred for 4 h. The mixture was acidified to near pH 2 with 1M Citric acid. The solution was transferred to an extraction funnel and the aqueous layer extracted with ethyl acetate (3×). The organic layers combined, dried with sodium sulfate and concentrated. LC/MS confirmed the major product was the desired mass. Additional purification was done by silica gel chromatography.

The Boc Intermediate was placed in a 20 mL vial and suspended in acetonitrile (3 mL). To this was added a solution of hydrochloric acid in dioxane (4N, 3 mL). The solution was stirred for 2 h and then concentrated under reduced pressure. The concentrate was taken up in water and applied to an ion exchange resin (Dowex-50). The capture material was washed with water and eluted with ammonium bicarbomnate. The enriched fractions with the amino acid were identified by TLC, pooled and lyophilized to afford the desired product. The product was confirmed by mass spectrometry.

Example 2. Preparation of Compounds of Formula III

Preparation of (2S)-2-amino-3-[(2-{[(2-azidoethoxy)carbonyl]amino}ethyl)sulfanyl]propanoic Acid (Formula III.1)

In a 4 mL vial with magnetic stirrer was placed cysteine (75 mg, 1 eq) and a solution of sodium carbonate (2.8M, 620 uL). To this was added 2-chloroethyl-N-(2-bromoethyl)carbamate (99 mg, 1.0 eq) in DMSO (620 uL). The vial was capped and allowed to stir for 8 h. Mass spectrometry indicated the formation of the desired s-alkylated intermediate. Following confirmation of the intermediate mass, sodium azide (120 mg) and DMSO (1 mL) were added, the vial was capped once again and the mixture heated to 60° C. overnight. Mass spectrometry indicated the successful formation of the desired mass. The pH of the crude mixture was adjusted to 2, lyophilized to a paste. The material was suspended in water and captured on an ion exchange resin (DOWEX-50), washed with water and eluted with ammonium hydroxide. The eluted fractions were pooled and lyophilized to afford the desired amino acid. The product was confirmed by mass spectrometry.

Preparation of (2S)-2-amino-3-[(2-{[(prop-2-yn-1-yloxy)carbonyl]amino}ethyl)sulfanyl]propanoic Acid (Formula III.2)

In a 4 mL vial with magnetic stirrer was placed cysteine (75 mg, 1 eq) and a solution of sodium carbonate (2.8M, 620 uL). To this was added prop-2-yn-1-yl N-(2-bromoethyl)carbamate (86 mg, 1.0 eq) in dioxane (620 ul). The vial was capped and allowed to stir overnight. Mass spectrometry indicated the formation of the desired S-alkylated product. The pH of the crude mixture was adjusted to 2, lyophilized to a paste. The material was suspended in water and captured on an ion exchange resin (DOWEX-50), washed with water and eluted with ammonium hydroxide. Enriched fractions were pooled and lyophilized to afford the desired amino acid. The product was confirmed by mass spectrometry.

Preparation of (2S)-2-amino-3-[(2-{[(prop-2-en-1-yloxy)carbonyl]amino}ethyl)sulfanyl]propanoic Acid (Formula III.3)

In a 4 mL vial with magnetic stirrer was placed cysteine (75 mg, 1 eq) and a solution of sodium carbonate (2.8M, 620 uL). To this was added prop-2-en-1-yl N-(2-bromoethyl)carbamate (88 mg, 1.0 eq) in dioxane (620 uL). The vial was capped and allowed to stir overnight. Mass spectrometry indicated the formation of the desired S-alkylated product. The pH of the crude mixture was adjusted to 2, lyophilized to a paste. The material was suspended in water and captured on an ion exchange resin (DOWEX-50), washed with water and eluted with ammonium hydroxide. Enriched fractions were pooled and lyophilized to afford the desired amino acid. The product was confirmed by mass spectrometry.

Preparation of (2S)-2-amino-3-({3-[(2-azidoethyl)carbamoyl]propyl}sulfanyl)propanoic Acid (Formula III.13)

In a 20 mL vial with magnetic stirrer was placed cysteine (75 mg, 1 eq) and a solution of sodium bicarbonate (1M, 1.7 mL). To this was added N-(2-azidoethyl)-4-bromobutanamide (86 mg, 1.0 eq) in dioxane (1.5 mLl). The vial was capped and allowed to stir for 8 h. Mass spectrometry indicated the formation of the desired S-alkylated product. The pH of the crude mixture was adjusted to 2 and applied to an ion exchange resin (DOWEX-50), washed with water and eluted with ammonium hydroxide. Fractions with the amino acid as identified by TLC, were pooled and lyophilized to afford the desired amino acid. The product was confirmed by Mass spectrometry.

Preparation of (2S)-2-amino-3-({3-[(prop-2-en-1-yl)carbamoyl]propyl}sulfanyl)propanoic Acid (Formula III.12)

In a 20 mL vial with magnetic stirrer was placed cysteine (285 mg, 1 eq) and a solution of sodium carbonate (2.8M, 1.2 mL). To this was added 4-bromo-N-(prop-2-en-1-yl) butanamide (333 mg, 1.0 eq). The vial was capped and allowed to stir overnight. Mass spectrometry indicated the formation of the desired s-alkylated product. The pH of the crude mixture was adjusted to 2, lyophilized to a paste. The material was suspended in water and captured on an ion exchange resin (DOWEX-50), washed with water and eluted with ammonium hydroxide. Enriched fractions were pooled and lyophilized to afford the desired amino acid. The product was confirmed by mass spectrometry.

Example 3. Preparation of Compounds of Formula V

Preparation of (2S)-2-amino-3-(2-{[(2-azidoethoxy)carbonyl]amino}acetamido)propanoic Acid (Formula V.1)

In a 4 mL vial with magnetic stirrer was placed 2-{[(2-chloroethoxy)carbonyl]amino}acetic acid (50 mg, 1 eq) and HBTU (105 mg, 1 eq) in 1 mL of DMF. The mixture was stirred for 15 min and then a solution of (2S)-3-amino-2-{[(tert-butoxy)carbonyl]amino}propanoic acid (66 mg, 1 eq) in DMF (1 mL) was added, followed by triethylamine (77 uL). The vial was capped and stirred for 4 h. The mixture was poured onto 250 mM citric acid and ethyl acetate and shaken. The layers were allowed to separate and the organic layer was retained. The aqueous layer was extracted two additional times with ethyl acetate. The organic layers were combined, dried with sodium sulfate, filtered and concentrated. Mass spectrometry indicated the formation of the desired product. The crude material was taken forward into the next step without additional purification.

The chloride intermediate was placed in a 20 mL vial and dissolved in DMSO (5 mL). Sodium azide (72 mg, 4 eq) was added and the vial was capped and stirred at 60° C. overnight. The mixture was poured onto 250 mM citric acid and ethyl acetate and shaken. The layers were allowed to separate and the organic layer was retained. The aqueous layer was extracted two additional times with ethyl acetate. The organic layers were combined, dried with sodium sulfate, filtered and concentrated. Mass spectrometry indicated the formation of the desired product. Additional purification could be accomplished by silica gel chromatography.

The boc group was removed by simple acidification. The Boc-azide intermediate was placed in a 20 mL vial and suspended in acetonitrile (2 mL). To this was added a solution of hydrochloric acid in dioxane (4N, 2 mL). The solution was stirred for 2 h and then concentrated under reduced pressure. The mixture was lyophilized to a paste. Additional purification with ion exchange resin (Dowex-50) afforded the desired amino acid. The product was confirmed by mass spectrometry.

Preparation of (2S)-2-amino-3-(2-{[(prop-2-entyloxy)carbonyl]amino}acetamido)propanoic Acid (Formula V.3)

In a 4 mL vial with magnetic stirrer was placed 2-{[(prop-2-en-1-yloxy)carbonyl]amino}acetic acid (50 mg, 1 eq) and HBTU (120 mg, 1 eq) in 1 mL of DMF. The mixture was stirred for 15 min and then a solution of (2S)-3-amino-2-{[(tert-butoxy)carbonyl]amino}propanoic acid (75 mg, 1 eq) in DMF (1 mL) was added, followed by triethylamine (88 uL). The vial was capped and stirred for 8 h. The mixture was partitioned between 250 mM citric acid and ethyl acetate. The organic layer was retained and the aqueous layer was extracted two additional times with ethyl acetate. The organic layers were combined, dried with sodium sulfate, filtered and concentrated. Mass spectrometry indicated the formation of the desired product. Additional purification could be accomplished by silica gel chromatography.

The Boc-protected intermediate was placed in a 20 mL vial and suspended in acetonitrile (2 mL). To this was added a solution of hydrochloric acid in dioxane (4N, 2 mL). The solution was stirred for 2 h and then concentrated under reduced pressure. The mixture was lyophilized to a paste. Additional purification by ion exchange resin (Dowex-50) afforded the desired amino acid. The product was confirmed by mass spectrometry.

Preparation of (2S)-2-amino-3-(2-{[(prop-2-yn-1-yloxy)carbonyl]amino}acetamido)propanoic Acid (Formula V.2)

In a 4 mL vial with magnetic stirrer was placed 2-{[(prop-2-yn-1-yloxy)carbonyl]amino}acetic acid (50 mg, 1 eq) and HBTU (121 mg, 1 eq) in 1 mL of DMF. The mixture was stirred for 15 min and then a solution of (2S)-3-amino-2-{[(tert-butoxy)carbonyl]amino}propanoic acid (76 mg, 1 eq) in DMF (1 mL) was added, followed by triethylamine (89 uL). The vial was capped and stirred for 8 h. The mixture was partitioned between 250 mM citric acid and ethyl acetate. The organic layer was retained and the aqueous layer was extracted two additional times with ethyl acetate. The organic layers were combined, dried with sodium sulfate, filtered and concentrated. Mass spectrometry indicated the formation of the desired product. Additional purification could be accomplished by silica gel chromatography.

The Boc-protected intermediate, (2S)-2-{[(tert-butoxy)carbonyl]amino}-3-(2-{[(prop-2-yn-1-yloxy)carbonyl]amino}acetamido)propanoic acid was placed in a 20 mL vial and suspended in acetonitrile (2 mL). To this was added a solution of hydrochloric acid in dioxane (4N, 2 mL). The solution was stirred for 2 h and then concentrated under reduced pressure. The mixture was lyophilized to a paste. Additional purification by ion exchange resin (Dowex-50) afforded the desired amino acid. The product was confirmed by mass spectrometry.

Example 4. Preparation of Formula VII Analogs

Preparation of (2S)-2-amino-6-(2-azidopentanamido)hexanoic acid (Formula VII.1)

In a 20 mL vial with magnetic stirrer was placed 2-azidopentanoic acid (100 mg, 1 eq) and HBTU (266 mg, 1 eq) in 3 mL of DMF. The mixture was stirred for 15 min and then a solution N-Boc-Lysine (200 mg, 1 eq) in DMF (3 mL) was added, followed by triethylamine (195 uL). The vial was capped and stirred for 8 h. The mixture was partitioned between 250 mM citric acid and ethyl acetate. The organic layer was retained and the aqueous layer was extracted two additional times with ethyl acetate. The organic layers were combined, dried with sodium sulfate, filtered and concentrated. Mass spectrometry indicated the formation of the desired intermediate. Additional purification was conducted via silica gel chromatography.

Intermediate was placed in a 20 mL vial and suspended in acetonitrile (2 mL). To this was added a solution of hydrochloric acid in dioxane (4N, 2 mL). The solution was stirred for 2 h and then concentrated under reduced pressure. The mixture was lyophilized. Additional purification by ion exchange resin (Dowex-50) afforded the desired amino acid. The product was confirmed by mass spectrometry.

Example 5. Preparation of Formula VIII Analogs

Preparation of (2S)-2-amino-3-(4-azido-2-{[(prop-2-en-1-yloxy)carbonyl]amino}butanamido)propanoic Acid (Formula VIII.1)

In a 4 mL vial with magnetic stirrer was placed (2S)-3-(4-azido-2-{[(prop-2-en-1-yloxy)carbonyl]amino}butanamido)-2-{[(tert-butoxy)carbonyl]amino}propanoic acid (65 mg, 1 eq) and HBTU (108 mg, 1 eq) in 1 mL of DMF. The mixture was stirred for 15 min and then a solution of (2S)-3-amino-2-{[(tert-butoxy)carbonyl]amino}propanoic acid (68 mg, 1 eq) in DMF (1 mL) was added, followed by triethylamine (79 uL). The vial was capped and stirred for 4 h. The mixture was poured onto 250 mM citric acid and ethyl acetate, shaken and the organic layer retained. The aqueous layer was extracted two additional times with ethyl acetate. The organic layers were combined, dried with sodium sulfate, filtered and concentrated. Mass spectrometry indicated the formation of the desired product. Additional purification could be accomplished by silica gel chromatography.

The Boc-protected intermediate was placed in a 20 mL vial and suspended in acetonitrile (2 mL). To this was added a solution of hydrochloric acid in dioxane (4N, 2 mL). The solution was stirred for 2 h and then concentrated under reduced pressure. The mixture was lyophilized. Additional purification by ion exchange resin (Dowex-50) afforded the desired amino acid. The product was confirmed by mass spectrometry.

Example 6. Translational Testing with a GFP Assay

An in vitro cell based assay was developed to assess the compatibility of the pylRS/tRNA pair and the pyrrolysine analogs of the present invention (nnAAs) by and the efficiency of nnAAs integration into a target protein. For this, HEK293 cells stably expressing pylRS (SEQ ID NO 4) were transiently transfected with plasmids for the expression of tRNApyl (SEQ ID NO 7) and a reporter construct encoding GFPY40 (containing amber codon in place of tyrosine at amino acid residue number 40 (where 1 is the initiator methionine)) (SEQ ID NOs 10 and 11) using standard transfection protocols. Transfected cells were incubated with nnAAs at 2 mM for 2-3 days GFP production was analyzed qualitatively by visual inspection under the microscope. The GFP fluorescence was quantified by flow cytometry using an Accuri flow cytometer and the geometric mean of the fluorescent cells determined.

This cell based assay was used to determine whether the different nnAAs were suitable substrates for the pylRS and allowed its translation into a target protein. Cells expressing the PylRS/tRNApyl pair and containing a vector encoding the GFPY40 reporter gene were incubated in the presence of the nnAAs. nnAAs that are readily utilized by the PylRS/tRNApyl pair support the translation of the nnAA into the amber site of GFP and allow read-through of the gene producing full length GFP (fluorescent protein). The fluorescence intensity of the cells depends on the efficiency of nnAA incorporation. Thus, nnAAs that are poorly utilized produce weakly fluorescent or non-fluorescing cells. Microscopic observation identified a number of nnAAs usable by the pylRS (Table 1, Positive GFP). Furthermore, the relative expression levels in each sample was compared to those generated by substrates known to be efficiently utilized by pylRS. Formula IA.1 (MFI=931,289), Formula IA.2 (MFI=1,676,250) and Formula IA.3 (MFI=2,250,000) (see Table 1) supported high levels of GFP expression with a geometric mean.

Analog Formulas IA.4, IA.5, III.1, III.2, III.3, III.12, III.13, V.1, V.2, V.3, VII.1 of the present invention were found by the inventors to be incorporated in the GFP reporter gene and yield green cells under the experimental conditions used. Among these, analogs Formula III.1 (MFI=1,989,750), Formula III.2 (MFI=1,847,250) and Formula III.3, (MFI=2,187,000) (see Table 2) supported high levels of GFP expression and represent analogues that are efficiently utilized by the pylRS/tRNA pair under the experimental conditions tested.

TABLE 1

Formula I analog GFP results

| Formula | IUPAC Name | Positive GFP | MFI |
|---|---|---|---|
| 1A.1 | (2S)-2-amino-6-{[(2-azidoethoxy)carbonyl]amino}hexanoic acid | Yes | 931289 |
| 1A.2 | (2S)-2-amino-6-{[(prop-2-yn-1-yloxy)carbonyl]amino}hexanoic acid | Yes | 1676250 |
| 1A.3 | (2S)-2-amino-6-{[(prop-2-en-1-yloxy)carbonyl]amino}hexanoic acid | Yes | 2250000 |
| 1A.4 | (2S)-2-amino-6-{[(2-azidoethyl)carbamoyl]amino}hexanoic acid | Yes | 254250 |

TABLE 2

Formula III analog GFP results

| Formula | IUPAC Name | Positive GFP Assay | MFI |
|---|---|---|---|
| III.1 | (2S)-2-amino-3-[(2-{[(2-azidoethoxy)carbonyl]amino}ethyl)-sulfanyl]propanoic acid | Yes | 1989750 |
| III.2 | (2S)-2-amino-3-[(2-{[(prop-2-yn-1-yloxy)carbonyl]amino}ethyl)sulfanyl]propanoic acid | Yes | 1847250 |
| III.3 | (2S)-2-amino-3-[(2-{[(prop-2-en-1-yloxy)carbonyl]amino}ethyl)sulfanyl]propanoic acid | Yes | 2187000 |
| III.13 | (2S)-2-amino-3-({3-[(2-azidoethyl)carbamoyl]propyl}-sulfanyl)-propanoic acid | Yes | |
| III.12 | (2S)-2-amino-3-({3-[(prop-2-en-1-yl)carbamoyl]propyl}sulfanyl)-propanoic acid | Yes | |

TABLE 3

Formula V analog GFP results

| Formula | IUPAC Name | Positive GFP Assay | MFI |
|---|---|---|---|
| V.1 | (2S)-2-amino-3-(2-{[(2-azidoethoxy)carbonyl]amino}acetamido)-propanoic acid | Yes | |
| V.3 | (2S)-2-amino-3-(2-{[(prop-2-en-1-yloxy)carbonyl]amino}acetamido)-propanoic acid | Yes | |

TABLE 4

Formula VII analogs GFP results

| Formula | IUPAC Name | Positive GFP Assay | MFI |
|---|---|---|---|
| VII.1 | (2S)-2-amino-6-(2-azidopentanamido)-hexanoic acid | Yes | |

TABLE 5

Formula VIII analogs GFP results

| Formula | IUPAC Name | Positive GFP Assay | MFI |
|---|---|---|---|
| VIII.1 | (2S)-2-amino-3-(4-azido-2-{[(prop-2-en-1-yloxy)carbonyl]amino}butanamido)-propanoic acid | Yes | |

Example 7. Site Specific Insertion of Pyrrolysine Analogs in Antibodies and Conjugation Construction and Expression of Anti-Her2 Antibody Containing Pyrrolysine Analog Residues A full length anti-Her2 antibody containing two non natural amino acids (one in each heavy chain) (4D5-2AZ ab) (SEQ ID NO 15) was expressed in mammalian cells. CHO cells stably expressing Her2 antibody encoding amber sites at position K274 (SEQ ID NO 14) and expressing the pylRS/tRNA pair were exposed to nnAA of Formula III.1 and Formula IA.1. The nnAAs of Formula III.1 or Formula IA.1, containing an azide moiety, were incorporated at the heavy chain position K274 and purified by affinity chromatography using either protein A resin (GE Healthcare) or by IgSelect (GE Healthcare, 17096901). The purified material was then concentrated and subjected to a conjugation reaction.

An antibody directed to the extracellular domain of Her2/neu was generated by cloning the variable regions of both the heavy and light chains of the mouse antibody 4D5 into vectors containing genes encoding human IgG. The variable regions of 4D5 were generated by gene synthesis using overlapping oligomers and cloned into the human IgG1 frameworks encoded by pFUSE-CHIg-hG1 (IgG1 heavy chain; gamma) (SEQ ID NOs 12 and 13) and pFUSE-CHLIg-hK (light chain; kappa; Invivogen)(SEQ ID NOs 16 and 17) to generate a mouse-human hybrid. An amber codon was introduced into the heavy chain (gamma) at position K274 by site directed mutagenesis (SEQ ID NOs 14 and 15). Clones containing the amber codon were identified by DNA sequencing. To generate an integrating construct the promoters and ORF for the heavy chain was amplified by PCR and cloned by restriction enzyme digestion and ligation into pOptivec (Life Technologies). The light chain and a single copy of the tRNA were joined by two step PCR method using overlapping oligomers and cloned into available sites into the pOptivec plasmid containing the heavy chain. The construct was then transfected into a CHO-DG44 cell line containing the pylRS/tRNA pair and transfectants selected by virtue of their growth in medium lacking hypoxanthine and thymidine. Selected cells were then cloned and high IgG expressors capable of efficient introduction of nnAAs into amber codons (expression of full length IgG) isolated. The selected cell line was utilized to generate IgG containing the nnAAs described above. The cells were grown to a density of $1-2\times10^6$ cells/mL in Excel DHFR-medium (Sigma-Aldrich) and nnAA of Formula III.1 or Formula IA.1 added to culture to a final concentration of 1 mM. Cells were incubated for 5 days and IgG purified from the growth medium. Supernatants were harvested and subjected to centrifugation to collect suspended cells and other debris. The supernatant was then filtered through a 0.22 um filter to remove any particulate material prior to application to a chromatography column. The filtered supernatant was applied to a 1 mL-5 mL prepacked HiTrap protein A Sepharose at 1-5 mL/min flow rate using an AKTA chromatography system. The bound material and resin were washed with PBS to remove loosely bound proteins and the bound material eluted with 100 mM glycine (pH 3.0) at a flow rate of 1 mL/min. Peak fractions containing the target protein were neutralized with 0.1 fraction volumes of 1M Tris-HCl (pH8.0). All constructs were dialyzed to PBS at 4° C. for 16 hours into the final phosphate buffer. The antibody with Formula III.1 as nnAA incorporated into both of its heavy chains at position 274 was called "4D5-2AzAb-HC-274-(2S)-2-amino-3-[(2-{[(2-azidoethoxy)carbonyl]amino}ethyl)sulfanyl] propanoic acid".

PEGylation of 4D5-2AzAb-HC-274-(2S)-2-amino-3-[(2-{[(2-azidoethoxy)carbonyl]amino}ethyl)sulfanyl]propanoic Acid In a 200 uL PCR tube was placed a solution of 4D5-2AzAb-HC274-(2S)-2-amino-3-[(2-{[(2-azidoethoxy)carbonyl]amino}ethyl)sulfanyl]propanoic acid (Formula III.1) (100 uL, 0.05 mg/mL) followed by a solution of 20KPEG cyclooctyne (33.3, 60 mg/mL). The solution was mixed vigorously on a vortexer and allowed to incubate overnight. The mixture was diluted to 200 uL and applied to Protein-A magnetic beads. The mixture was vortexed and allowed to rotate to mix the beads for 90 min. The beads were immobilized and the run through material disposed. The beads were washed with PBS (2x) and then suspended in reducing gel buffer. Vortexed and then heated to 95 C for 3 min. The suspension was loaded directly onto an SDS-PAGE gel. Commassie staining of the SDS-PAGE gel indicated the selective PEGylation of the Heavy chain (FIG. 1, lane 2).

REFERENCES

Fekner, T., Li, X., & Chan, M. K. (2010). Pyrrolysine Analogs for Translational Incorporation into Proteins. *European Journal of Organic Chemistry*, 4171-4179.

Kavran, J. M., Gundllapalli, S., O'Donoghue, P., Englert, M., Soll, D., & Steltz, T. A. (2007). Structure of pyrrolysyl-tRNA synthetase, an archaeal enzyme for genetic code innovation. *Proceedings National Academy of Sciences*, 104 (27), 11268-11273.

Kobayashi, T., Yanagisawa, T., Sakamoto, K., & Yokoyama, S. (2009). Recognition of Non-a-amino Substrates by Pyrrolysyl-tRNA Synthetase. *J. Mol. Biol.* (1352-1360), 385.

Liu, Chang C, and Peter G Schultz. "Adding New Chemistries to the Genetic Code." *Annual Review of Biochemistry*, 2010: 413-444.

Chan, Michael K, Tomasz Fekner, Xin Li, Marianne Lee, and Jennifer J Ottesen. International Patent WO2011/044255A1. 2011.

Nguyen, D. P., Lusic, H., Neumann, H. K., Deiters, A., & Chin, J. W. (2009). Genetic Encoding and Labeling of Aliphatic Azides and Alkynes in Recombinant Proteins via a Pyrrolysyl-tRNA Synthetase/tRNAcua Pair and Click Chemistry. *Journal of the American Chemical Society,* 8720-8721.

Yanagisawa, T., Ishii, R., Fukunaga, R., Kobayashi, T., Sakamoto, K., & Yokoyama, S. (2008). Crystallographic Studies on Multiple Conformational States of Active-site loops in Pyrrolysyl-tRNA synthetase. *J. Mol. Biol.,* 378, 634-652.

Yanagisawa, T., Ishii, R., Fukunaga, R., Kobayashi, T., Sakamoto, K., & Yokoyama, S. (2008). Multistep Engineering of Pyrrolysyl-tRNA Synthetase to Genetically Encode Ne-(o-Azidobenzyloxycarbonyl)lysine for Site Specific Protein Modification. *Chemistry and Biology,* 15, 1187-1197.

Yanagisawa, T., Sumida, T., Ishii, R., & Yokoyama, S. (2013). A novel crystal fom of pyrrolysyl-tRNA synthetase reveals the pre- and post-aminoacyl-tRNA synthesis conformational states of the adenylate and aminoacyl moieties and an asparagine residue in the catalytic site. *Acta Crystallographica Section D, D*69, 5-15.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A pyrrolysine analogue of formula X:

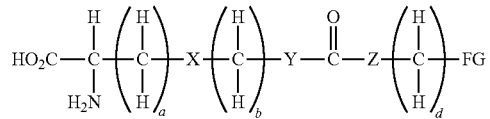

wherein

X=O or S;

Y=CH$_2$, NH, O or S;

Z=CH$_2$, CH—NH$_2$, CH—OH, NH, O or S;

FG azide, alkene, alkyne, ketone, ester, or cycloalkyne;

a=an integer 1-7;

b=an integer 1-7 save that when Z is NH, O or S then b is an integer 2-7;

provided that a+h is in the range 2-8;

and d=an integer 1-4.

2. A pyrrolysine analogue according to claim 1 which is a pyrrolysine analogue of formula III:

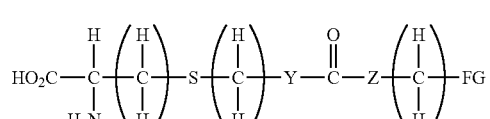

wherein a, b, Z, d and FG are as defined in claim 1.

3. A pyrrolysine analogue according to claim 2 selected from

Formula III.1
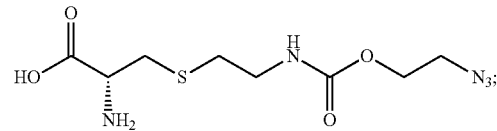

Formula III.2
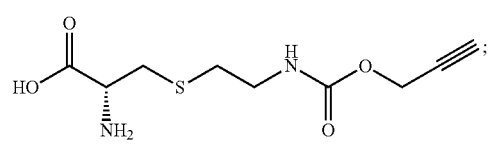

Formula III.3
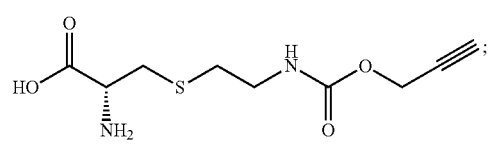

Formula III.4
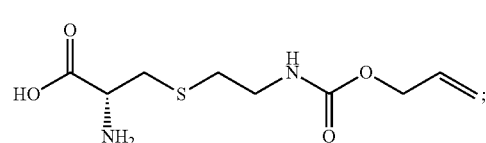

Formula III.5
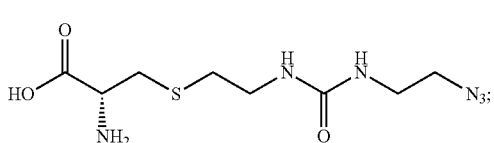

-continued

Formula III.6
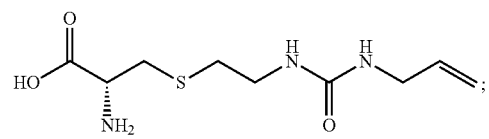

Formula III.7
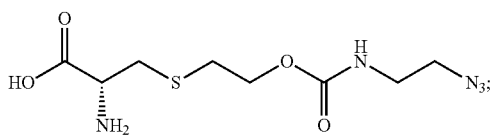

Formula III.8
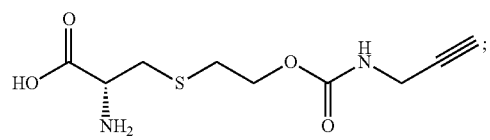

Formula III.9
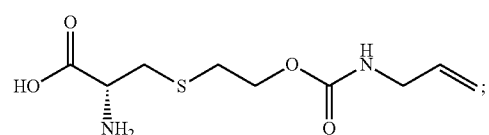

Formula III.10
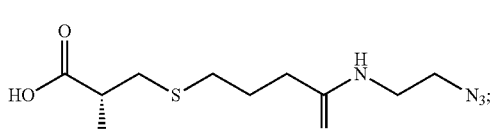

Formula III.11
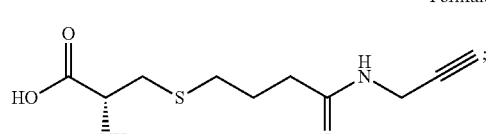

Formula III.12
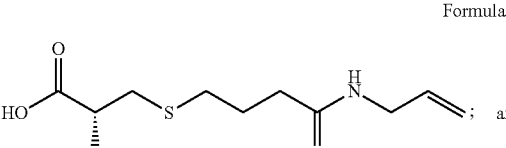

Formula III.13
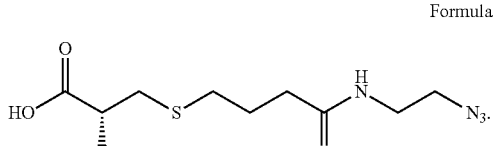

4. A pyrrolysine analogue according to claim 1 which is a pyrrolysine analogue of
Formula IV:

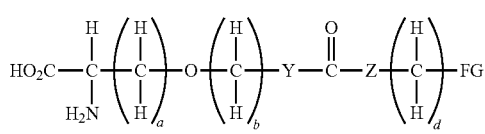

wherein a, b, Y, Z, d and FG are as defined in claim 1.

5. A pyrrolysine analogue according to claim 4 selected from

Formula IV.1
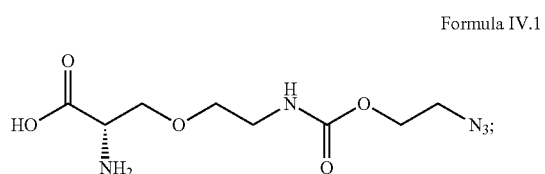

Formula IV.2
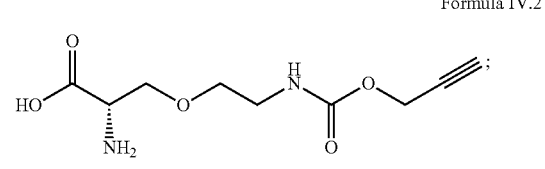

Formula IV.3
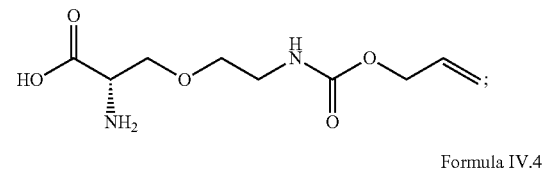

Formula IV.4
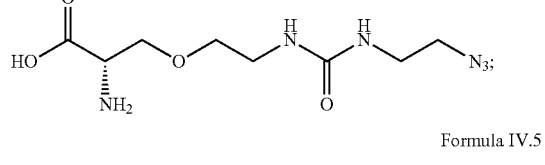

Formula IV.5
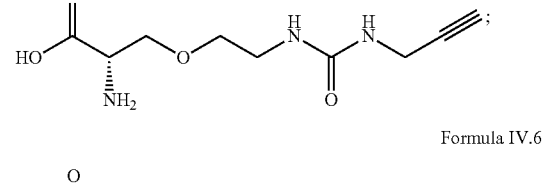

Formula IV.6
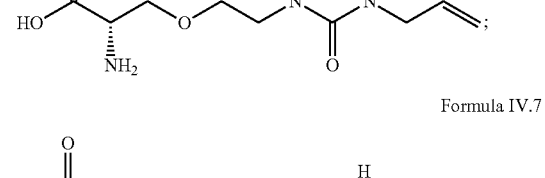

Formula IV.7
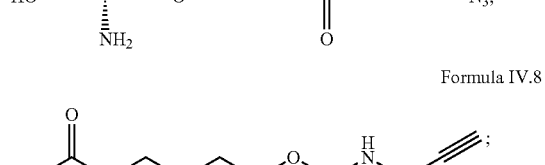

Formula IV.8
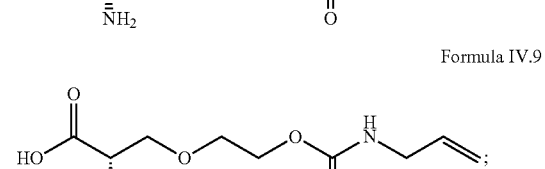

Formula IV.9

-continued

Formula IV.10
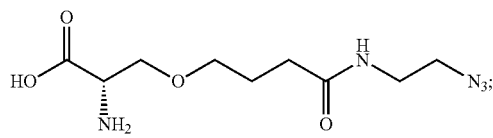

Formula IV.11
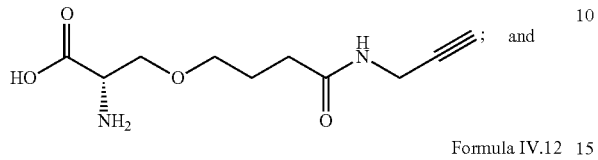

Formula IV.12
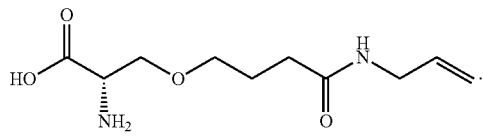

6. A pyrrolysine analogue of formula I:

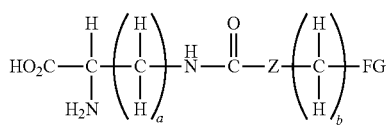

wherein
Z=bond, CH$_2$, CH—NH$_2$, CH—OH, NH, O, S or CH—NH$_2$;
a is an integer 3-7;
b is 0 or an integer 1-7; and
FG=azide, alkene, alkyne, ketone, ester, or cycloalkyne;
with the provisos that:
when a represents 4 and Z represents O, —(CH$_2$)$_b$-FG does not represent —CH$_2$—C≡CH, —CH$_2$CH$_2$—N$_3$, —CH$_2$—CH=CH$_2$ or —CH$_2$-Ph;
when a represents 4 and Z represents O, —(CH$_2$)$_b$-FG does not represent —CH$_2$CH$_2$CH$_2$—C(=O)CH$_3$ or —CH$_2$CH$_2$CH$_2$—CH=CH$_2$;
when a represents 4, Z represents a bond and b represents 0, —(CH$_2$)$_b$-FG does not represent —C(=O)Bn or —C(=O)Me; and
when a represents 4 and Z represents a bond, —(CH$_2$)$_b$-FG does not represent —CH$_2$CH$_2$—C≡CH.

7. A pyrrolysine analogue according to claim 6 selected from

Formula IA.4
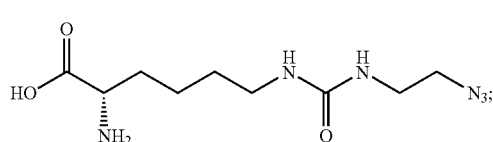

Formula IA.5
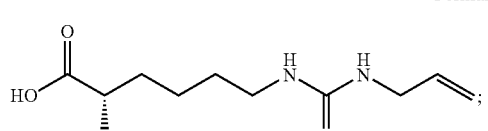

Formula IA.6
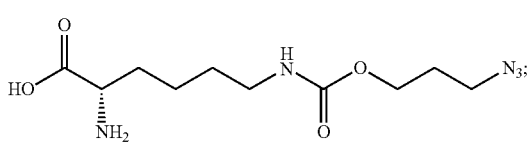

Formula IA.7
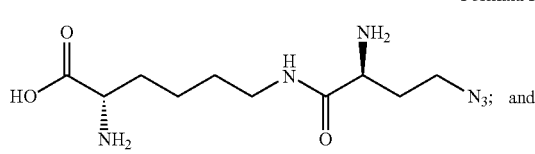

Formula IA.9
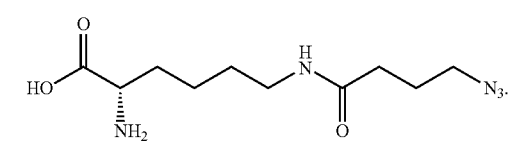

8. A pyrrolysine analogue according to claim 6 selected from

Formula IB.1
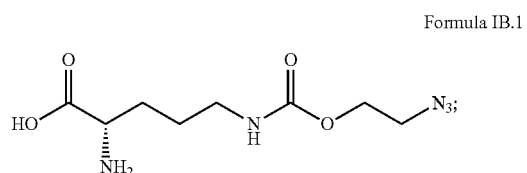

Formula IB.2
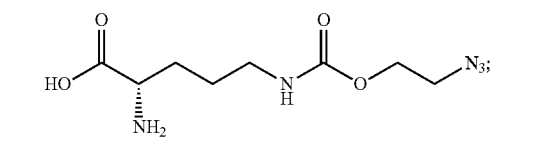

Formula IB.3
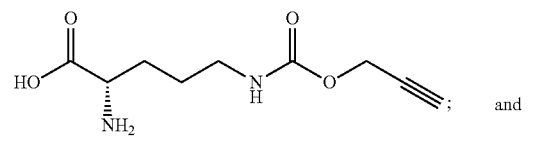

9. A pyrrolysine analogue of formula II:

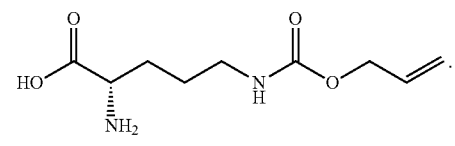

wherein
Z=CH$_2$, CH—NH$_2$, CH—OH, NH, O or S;
FG=azide, alkene, alkyne, ketone, ester, aryl or cycloalkyne;
a=an integer 3 or 5-7; and
b=an integer 1-4.

10. A pyrrolysine analogue of formula V:

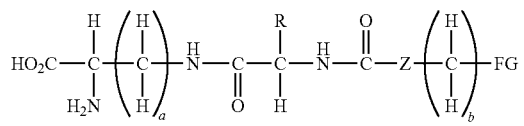

wherein
R=the side chain of one of the 20 natural amino acids;
Z=CH$_2$, CH—NH$_2$, CH—OH, NH, O or S;
FG=azide, alkene, alkyne, ketone, ester, aryl or cycloalkyne;
a=1; and
b=an integer 1 to 4.

11. A pyrrolysine analogue according to claim 10 selected from

Formula V.1
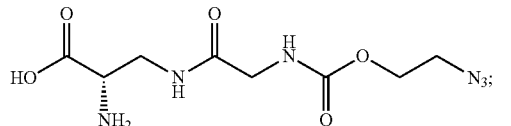

Formula V.2
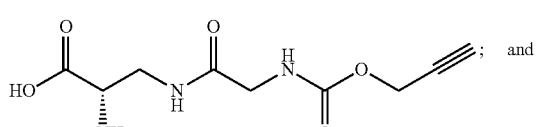

Formula V.3
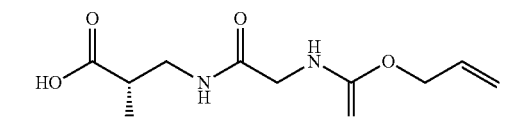

12. A pyrrolysine analogue of formula VI:

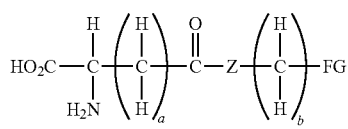

wherein
Z=CH$_2$, CH—NH$_2$, CH—OH, NH, O or S;
PG=azide, alkene, alkyne, ketone, ester, or cycloalkyne;
a=4 or 5; and
b=an integer 1 to 4.

13. A pyrrolysine analogue according to claim 12 selected from

Formula VI.1
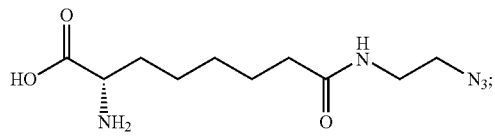

Formula VI.2
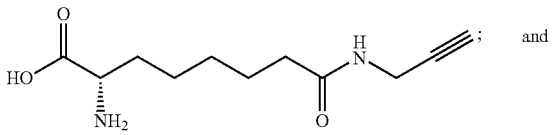

and

Formula VI.3
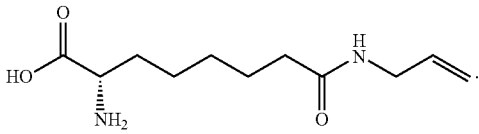

14. A pyrrolysine analogue of formula VII:

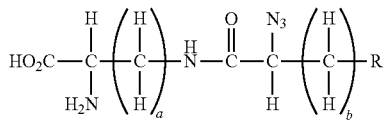

wherein
R=alkyl, alkenyl, cycloalkyl, aryl, heteroaryl or heterocyclyl;
a=an integer 1 to 7; and
b=an integer 1 to 3.

15. A pyrrolysine analogue according to claim 14 which is:

Formula VII.1
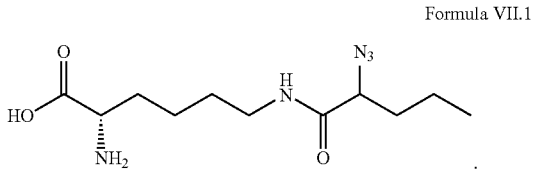 [SMILES: CCCC(N=[N+]=[N-])C(=O)NCCCC[C@H](N)C(=O)O]

16. A pyrrolysine analogue of formula VIII:

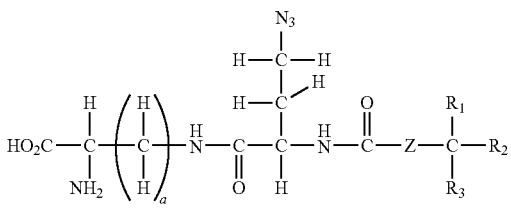

wherein
Z=CH$_2$, CH—NH$_2$, CH—OH, NH, O or S;
R$_1$=H, alkyl, alkenyl, cycloalkyl, cycloalkenyl, aryl, heteroaryl or heterocyclyl;
R$_2$=alkyl, alkenyl, cycloalkyl, cycloalkenyl, aryl, heteroaryl or heterocyclyl;
R$_3$=H, alkyl, alkenyl, cycloalkyl, cycloalkenyl, aryl, heteroaryl or heterocyclyl; and
a=1.

17. A pyrrolysine analogue according to claim 16 selected from

Formula VIII.1

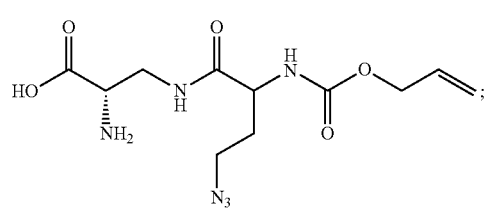

Formula VIII.2

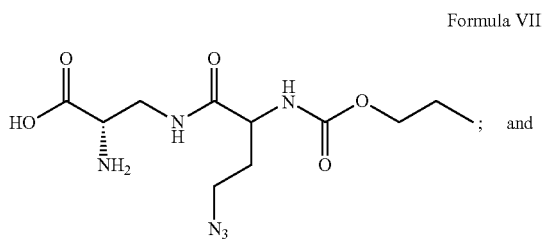
; and

Formula VIII.3

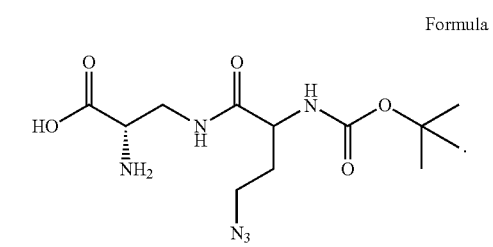
.

18. A pyrrolysine analogue according to claim 3 wherein the pyrrolysine analogue is Formula III.1

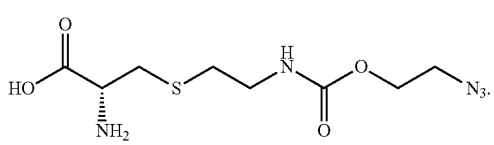
.

19. A pyrrolysine analogue according to claim 3, wherein the pyrrolysine analogue is Formula III.2

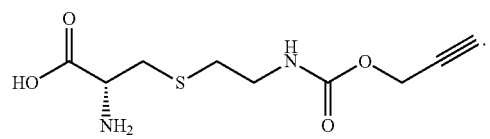
.

20. A pyrrolysine analogue according to 3, wherein the pyrrolysine analogue is

Formula III.3

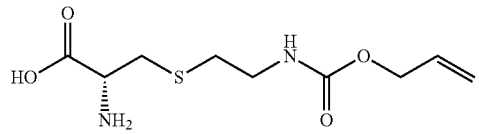
.

21. A pyrrolysine analogue according to 3, wherein the pyrrolysine analogue is

Formula III.12

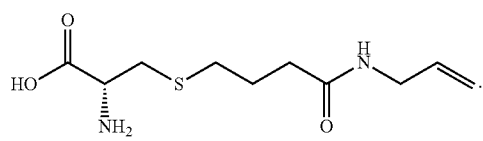
.

22. A pyrrolysine analogue according to 3, wherein the pyrrolysine analogue is

Formula III.13

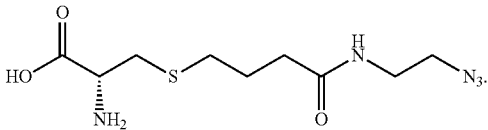
.

23. A pyrrolysine analogue according to 7, wherein the pyrrolysine analogue is

Formula IA.4

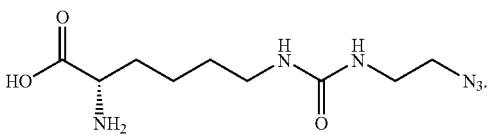
.

24. A pyrrolysine analogue according to 11, wherein the pyrrolysine analogue is

Formula V.1

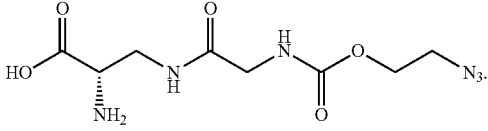
.

25. A pyrrolysine analogue according to 11, wherein the pyrrolysine analogue is
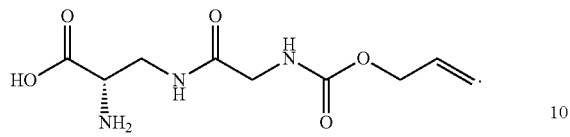
Formula V.3
26. A pyrrolysine analogue according to 17, wherein the pyrrolysine analogue is
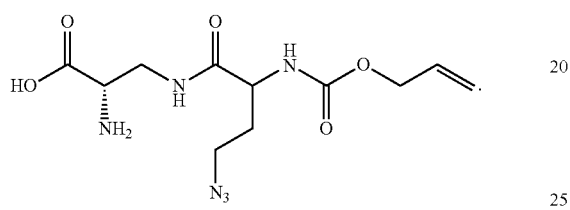
Formula VIII.1
* * * * *